(12) United States Patent
Raffel et al.

(10) Patent No.: US 10,259,781 B2
(45) Date of Patent: Apr. 16, 2019

(54) IMAGING AGENTS

(71) Applicant: THE REGENTS OF THE UNIVERSITY OF MICHIGAN, Ann Arbor, MI (US)

(72) Inventors: David M. Raffel, Ann Arbor, MI (US); Yong-Woon Jung, Ann Arbor, MI (US); Keun-Sam Jang, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 0 days.

(21) Appl. No.: 15/891,819

(22) Filed: Feb. 8, 2018

(65) Prior Publication Data
US 2018/0230088 A1 Aug. 16, 2018

Related U.S. Application Data

(63) Continuation of application No. 15/367,856, filed on Dec. 2, 2016, which is a continuation of application No. 14/428,876, filed as application No. PCT/US2013/061681 on Sep. 25, 2013.

(60) Provisional application No. 61/705,477, filed on Sep. 25, 2012.

(51) Int. Cl.
| | |
|---|---|
| *A61K 51/00* | (2006.01) |
| *A61M 36/14* | (2006.01) |
| *C07C 279/08* | (2006.01) |
| *A61K 31/155* | (2006.01) |
| *A61K 51/04* | (2006.01) |
| *C07B 59/00* | (2006.01) |
| *C07C 277/06* | (2006.01) |
| *C07C 277/08* | (2006.01) |
| *C07C 279/06* | (2006.01) |

(52) U.S. Cl.
CPC .......... *C07C 279/08* (2013.01); *A61K 31/155* (2013.01); *A61K 51/04* (2013.01); *C07B 59/001* (2013.01); *C07B 59/002* (2013.01); *C07C 277/06* (2013.01); *C07C 277/08* (2013.01); *C07C 279/06* (2013.01); *C07B 2200/05* (2013.01)

(58) Field of Classification Search
CPC .......................... C07C 279/06; C07B 2200/05
USPC ........................................................ 424/1.89
See application file for complete search history.

(56) References Cited

U.S. PATENT DOCUMENTS

| | | | |
|---|---|---|---|
| 4,584,187 | A | 4/1986 | Wieland et al. |
| 4,622,217 | A | 11/1986 | Wieland |
| 4,864,138 | A | 9/1989 | Mullani |
| 5,451,789 | A | 9/1995 | Wong et al. |
| 5,453,623 | A | 9/1995 | Wong et al. |
| 6,674,083 | B2 | 1/2004 | Tanaka et al. |
| 6,822,240 | B2 | 11/2004 | Francke et al. |
| 7,534,415 | B2 | 5/2009 | Pinnavaia et al. |
| 7,534,418 | B2 | 5/2009 | Raffel et al. |
| 2006/0100225 | A1 | 5/2006 | Chen et al. |
| 2006/0127309 | A1 | 6/2006 | Raffel et al. |
| 2010/0221182 | A1 | 9/2010 | Puroht et al. |
| 2011/0144344 | A1 | 6/2011 | Woodcraft |

FOREIGN PATENT DOCUMENTS

| | | |
|---|---|---|
| WO | WO 2008083056 A2 | 7/2008 |
| WO | WO 2011143360 A2 | 11/2011 |

OTHER PUBLICATIONS

Barron et al. J Med. Chem. 6, 1963, 705-711.*
Augstein, et al., "Adrenergic Neurone Blocking Agents Derived from 1,4-Benzodioxan", J. Med. Chem., 1965, 8 (4), pp. 446-456.
Bolster, et al., "Synthesis of DL-[1-11C]methionine." Int J. Rad Appl Instrum A. 1986;37(10):1069-1070.
Broadley KJ, Autonomic Pharmacology. London: Taylor & Francis (1996), TOC only.
Comar, et al., "Labelling and metabolism of methionine-methyl-11 C." Eur J Nucl Med. 1976;1(1):11-14.
Dahmen, et al., "A novel solid-phase synthesis of highly diverse guanidines: reactions of primary amines attached to the T2 linker." Org Lett. Nov. 16, 2000;2(23):3563-3565.
Ding, et al., "Synthesis of high specific activity 6-[18F]fluorodopamine for positron emission tomography studies of sympathetic nervous tissue." J Med Chem. Feb. 1991;34(2):861-863.
Garg, et al., "Synthesis and preliminary evaluation of para- and meta-[18F]fluorobenzylguanidine." Nucl Med Biol. Jan. 1994;21(1):97-103.
Ichikawa, et al.,"Synthesis of Blastidic Acid and Cytosinine, Two Components of Blasticidin S", Synlett 2001, 11, 1763-1766.
Jacobson, et al., "Myocardial iodine-123 meta-iodobenzylguanidine imaging and cardiac events in heart failure. Results of the prospective ADMIRE-HF (AdreView Myocardial Imaging for Risk Evaluation in Heart Failure) study." J Am Coll Cardiol. May 18, 2010;55(20):2212-2221.
Jang, et al., "Synthesis and bioevaluation of [(18)F]4-fluoro-m-hydroxyphenethylguanidine ([(18)F]4F-MHPG): a novel radiotracer for quantitative PET studies of cardiac sympathetic innervation." Bioorg Med Chem Lett. Mar. 15, 2013;23(6):1612-1616.
Keen, et al., "In vivo cerebral protein synthesis rates with leucyl-transfer RNA used as a precursor pool: determination of biochemical parameters to structure tracer kinetic models for positron emission tomography." J Cereb Blood Flow Metab. Aug. 1989;9(4):429-445.

(Continued)

*Primary Examiner* — Michael G. Hartley
*Assistant Examiner* — Sean R Donohue
(74) *Attorney, Agent, or Firm* — Casimir Jones, S.C.; Thomas A. Isenbarger

(57) ABSTRACT

Provided herein is technology relating to imaging agents and particularly, but not exclusively, to methods of manufacturing fluorine-18-labeled phenethylguanidines and uses thereof.

12 Claims, 15 Drawing Sheets

(56) References Cited

OTHER PUBLICATIONS

Kline, et al., "Myocardial imaging in man with I-123 meta-iodobenzylguanidine." J Nucl Med. Feb. 1981;22(2):129-132.
Koser, et al., "One-step .alpha.-tosyloxylation of ketones with [hydroxy(tosyloxy)iodo]benzene" J. Org. Chem., 1982, 47 (12), pp. 2487-2489.
Lange, et a., "EM reconstruction algorithms for emission and transmission tomography." J Comput Assist Tomogr. Apr. 1984;8(2):306-316.
Langer, et al., "High specific radioactivity (1R,2S)-4-[(18)F]fluorometaraminol: a PET radiotracer for mapping sympathetic nerves of the heart." Nucl Med Biol. Apr. 2000;27(3):233-238.
Langer, et al.,"Synthesis of high-specific-radioactivity 4- and 6-[18F]fluorometaraminol-PET tracers for the adrenergic nervous system of the heart." Bioorg Med Chem. Mar. 2001;9(3):677-694.
Lynn, et al., "Portrayal of pheochromocytoma and normal human adrenal medulla by m-[123I]iodobenzylguanidine: concise communication." J Nucl Med. Apr. 1984;25(4):436-440.
Patlak, et al., "Graphical evaluation of blood-to-brain transfer constants from multiple-time uptake data. Generalizations." J Cereb Blood Flow Metab. Dec. 1985;5(4):584-590.
Patani, et al. "Bioisosterism: A Rational Approach in Drug Design" Chem. Rev., 1996, 3147-3176.
Raffel, et al., "Radiolabeled phenethylguanidines: novel imaging agents for cardiac sympathetic neurons and adrenergic tumors." J Med Chem. May 3, 2007;50(9):2078-2088.
Ross, et al. "Nucleophilic $^{18}$F-Fluorination of Heteroaromatic Iodonium Salts with No-Carrier-Added [$^{18}$F]Fluoride", J. Am. Chem. Soc., 2007, 129 (25), pp. 8018-8025.
Shepp, et al., "Maximum likelihood reconstruction for emission tomography." IEEE Trans Med Imaging. 1982;1(2):113-1122.
Sisson, et al., "Scintigraphic localization of pheochromocytoma." N Engl J Med. Jul. 2, 1981;305(1):12-17.
Stabin, et al., "OLINDA/EXM: the second-generation personal computer software for internal dose assessment in nuclear medicine." J Nucl Med. Jun. 2005;46(6):1023-1027.
International Search Report and Written Opinion for PCT/US2013/061681, dated Jan. 24, 2014, 17 pages.
Valk, et al., "Spectrum of pheochromocytoma in multiple endocrine neoplasia. A scintigraphic portrayal using 131I-metaiodobenzylguanidine." Ann Intern Med. Jun. 1981;94(6):762-767.
Wieland, et al., "Myocardial imaging with a radioiodinated norepinephrine storage analog." J Nucl Med. Jan. 1981;22(1):22-31.
Wiesei, et al., "The transport of tyrosine into the human brain as determined with L-[1-11C]tyrosine and PET." J Nucl Med. Nov. 1991;32(11):2043-3049.
Yu, et al., "Evaluation of LMI1195, a novel 18F-labeled cardiac neuronal PET imaging agent, in cells and animal models." Circ Cardiovasc Imaging. Jul. 2011;4(4):435-443.
File History for related U.S. Appl. No. 60/877,211, filed Dec. 26, 2006.
Bovet et al., "Sympathomimetic action of some phenylethylenediamines" Comptes Rendus des Seances de la Societe de Biologie et de Ses Filiales (1939), 130, 1192-3.

* cited by examiner

IMAGING AGENTS

This application is a continuation of U.S. patent application Ser. No. 15/367,856, filed Dec. 2, 2016, now abandoned, which is a continuation of U.S. patent application Ser. No. 14/428,876, filed Mar. 17, 2015, now abandoned, which is a 371 U.S. National Phase Entry of International Patent Application No. PCT/US2013/061681, International Filing Date Sep. 25, 2013, which claims priority to expired U.S. Provisional Patent Application Ser. No. 61/705,477, filed on Sep. 25, 2012, each of which is incorporated herein by reference in its entirety.

STATEMENT REGARDING FEDERALLY SPONSORED RESEARCH OR DEVELOPMENT

This invention was made with government support under HL079540 awarded by the National Institutes of Health. The government has certain rights in the invention.

FIELD OF TECHNOLOGY

Provided herein is technology relating to imaging agents and particularly, but not exclusively, to methods of producing fluorine-18-labeled guanidine compounds.

BACKGROUND

Medical radionuclide imaging (e.g., nuclear medicine) is a key component of modern medical practice. This methodology involves the administration, typically by injection, of tracer amounts of a radioactive substance (e.g., radiotracer agents, radiotherapeutic agents, and radiopharmaceutical agents), which subsequently localize in the body in a manner dependent on the physiologic function of the organ or tissue system being studied. The radiotracer emissions, most commonly gamma photons, are imaged with a detector outside the body, creating a map of the radiotracer distribution within the body. When interpreted by an appropriately trained physician, these images provide information of great value in the clinical diagnosis and treatment of disease. Typical applications of this technology include detection of coronary artery disease (e.g., thallium scanning) and detection of cancerous involvement of bones (e.g., bone scanning). The overwhelming bulk of clinical radionuclide imaging is performed using gamma emitting radiotracers and detectors known as "gamma cameras".

Recent advances in diagnostic imaging, such as magnetic resonance imaging (MRI), computerized tomography (CT), single photon emission computerized tomography (SPECT), and positron emission tomography (PET), have made a significant impact in cardiology, neurology, oncology, and radiology. Although these diagnostic methods employ different techniques and yield different types of anatomic and functional information, this information is often complementary in the diagnostic process.

Imaging agents are generally classified as either being diagnostic or therapeutic in their application. Although diagnostic imaging agents have historically been a mainstay in the nuclear pharmacy industry, during the past decade there has been increased interest in the development and use of radioactive imaging agents for radiotherapy. This shift in focus has been elicited primarily from research involving combining radioactive isotopes with sophisticated molecular carriers. Because of radiation's damaging effect on tissues, it is important to target the biodistribution of radiopharmaceuticals as accurately as possible. Generally speaking, PET uses imaging agents labeled with positron-emitters such as $^{18}F$, $^{11}C$, $^{13}N$, $^{15}O$, $^{75}Br$, $^{76}Br$, and $^{124}I$; SPECT uses imaging agents labeled with single-photon-emitters such as $^{201}Tl$, $^{99m}Tc$, $^{123}I$, and $^{131}I$.

In the art, glucose-based and amino acid-based compounds have been used as imaging agents. Amino acid-based compounds are more useful in analyzing tumor cells due to their faster uptake and incorporation into protein synthesis. Of the amino acid-based compounds, $^{11}C$- and $^{18}F$-containing compounds have been used with success. $^{11}C$-containing radiolabeled amino acids suitable for imaging include, for example, L-[1-$^{11}C$]leucine (Keen et al. J. Cereb. Blood Flow Metab. 1989 (9)429-45; herein incorporated by reference in its entirety), L-[1-$^{11}C$]tyrosine (Wiesel et al. J. Nucl. Med. 1991 (32):2041-49; herein incorporated by reference in its entirety), L-[methyl-$^{11}C$]methionine (Comar et al. Eur. J. Nucl. Med. 1976 (1):11-14; herein incorporated by reference in its entirety) and L-[1-$^{11}C$]methionine (Bolster et al. Appl. Radiat. Isot. 1986 (37)1069-70; herein incorporated by reference in its entirety).

PET involves the detection of gamma rays in the form of annihilation photons from short-lived positron emitting radioactive isotopes including but not limited to $^{18}F$ with a half-life of approximately 110 minutes, $^{11}C$ with a half-life of approximately 20 minutes, $^{13}N$ with a half-life of approximately 10 minutes, and $^{15}O$ with a half-life of approximately 2 minutes, using the coincidence method.

For PET imaging studies of cardiac sympathetic innervation, carbon-11 ($^{11}C$) labeled compounds such as [$^{11}C$]meta-hydroxyephedrine (HED) are frequently used at major PET centers that have in-house cyclotrons and radiochemistry facilities. However, the nuclear medicine market has recently seen a substantial increase in stand-alone PET imaging centers that do not have cyclotrons and that primarily use 2-[$^{18}F$]fluoro-2-deoxy-D-glucose (FDG) for PET imaging of cancerous tumors.

SPECT, on the other hand, uses longer-lived isotopes including but not limited to $^{99m}Tc$ with a half-life of approximately 6 hours and $^{201}Tl$ with a half-life of approximately 74 hours. However, the resolution in present SPECT systems is lower than that presently available in PET systems.

Radio-iodinated meta-iodobenzylguanidine (MIBG) is a radiotracing agent that is used, for example, in nuclear medicine imaging studies of sympathetic nerve fibers in the human heart. Studies with MIBG allow clinicians to map the regional distribution of nerve fibers in the heart using imaging devices found in all nuclear medicine clinics. MIBG is also used for diagnostic imaging and radiotherapy of adrenergic tumors, such as neuroblastoma and pheochromocytoma.

New compounds that find use as imaging agents within nuclear medicine applications (e.g., PET imaging and SPECT imaging) have been described: for example, fluorine-18-labeled phenethylguanidines. See, e.g., U.S. Pat. No. 7,534,418, incorporated herein by reference in its entirety for all purposes.

While useful, introducing fluorine-18 into a phenyl ring moiety at high specific activities is a notoriously challenging radiolabeling task, especially in electron-rich aromatic systems. In the last 10 years, the use of diaryliodium salt precursors as a one-step method of introducing fluorine-18 into ring structures with high radiochemical yields has received considerable attention. Although this method has been used to prepare small model compounds with relatively simple structures, as the structures of the compounds being radiolabeled become more complex, radiochemical yields drop substantially. Accordingly, a need exists for methods of preparing fluorine-18 labeled phenethylguanidines and related compounds with high specific activity to make practical the production of such compounds on a commercial scale.

SUMMARY

Accordingly, provided herein is technology related to preparing ring-fluorinated guanidine radiotracers at high specific activities and high yields. As provided herein, a first step in particular embodiments of the technology uses a novel diaryliodonium salt precursor to introduce fluorine-18 into the ring structure, followed by removal of a N-Boc protecting group to yield a radiolabeled 4-[$^{18}$F]fluoro-meta-tyramine derivative in which the meta-hydroxy group remains protected by a benzyl group. This intermediate is then converted from a primary amine to a guanidine using N—N'-diBoc-5-chlorobenzotriazole. A further step deprotects the meta-hydroxy group to yield 4-[$^{18}$F]fluoro-meta-hydroxy-phenethylguanidine ([$^{18}$F]4F-MHPG; in some contexts, referred to by the name 4-[$^{18}$F]-MHPG).

As such, the technology relates to new methods of producing radioactive compounds; in particular, the methods relate to using a diaryliodium salt precursor to introduce fluorine-18 into the structure of a radiolabeled phenethylguanidine and related compounds and, in some embodiments, the methods relate to preparing a $^{18}$F-labeled primary amine intermediate followed by conversion to a guanidine. As provided herein, the methods are used to produce an exemplary novel compound, [$^{18}$F]4F-MHPG. The technology is contemplated to encompass related and generalized structures defining a unified set of novel diaryliodium salt precursors that are used to prepare $^{18}$F-labeled phenethylguanidines as disclosed in, e.g., U.S. Pat. No. 7,534,418, which is incorporated by reference in its entirety for all purposes.

Accordingly, provided herein is technology related in one aspect to compositions comprising an $^{18}$F-labeled phenethylguanidine having a structure according to

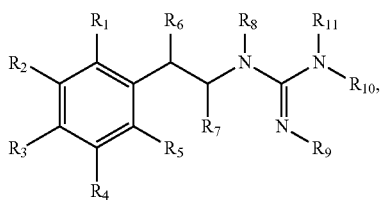

or a salt, a free base, or a combination thereof, wherein $R_1$, $R_2$, $R_3$, $R_4$, and $R_5$ are independently selected from the group consisting of $^{18}$F-labeled, $^{19}$F, hydrogen, halogen, hydroxyl, guanyl, alkoxy, haloalkoxy, $^{18}$F-labeled alkoxy, alkyl, haloalkyl, $^{18}$F-labeled alkyl, amine, and an amine comprising one or more protecting groups (e.g., a protected amine); $R_6$ and $R_7$ are independently selected from the group consisting of hydrogen, hydroxyl, alkoxy, haloalkoxy, $^{18}$F-labeled alkoxy, halogen, amino, alkyl, haloalkyl, and $^{18}$F-labeled alkyl; and $R_8$, $R_9$, $R_{10}$, and $R_{11}$ are independently selected from the group consisting of hydrogen, carbamate, cyclic carbamate, amide, cyclic amide, and a nitrogen-protecting group. In some embodiments of the composition, $R_8$ is a hydrogen, $R_9$ is a hydrogen, $R_{10}$ is a hydrogen, and/or $R_{11}$ is a hydrogen.

Also provided are embodiments related to compositions comprising a $^{18}$F-labeled phenethylguanidine, wherein the $^{18}$F-labeled phenethylguanidine is produced by a method comprising radiofluorinating an iodonium salt with an [$^{18}$F] fluoride ion source, e.g., as described by Reaction 1;

[Reaction Formula 1]

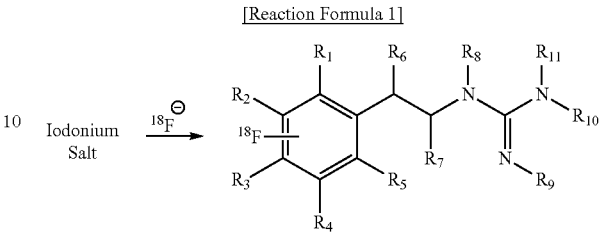

In some embodiments, the iodonium salt has a structure according to

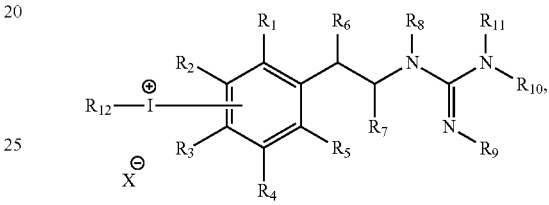

or is a salt, a free base, or a combination thereof, wherein $R_1$, $R_2$, $R_3$, $R_4$, and $R_5$ are independently selected from the group consisting of $R_{12}$—I, hydrogen, halogen, hydroxyl, guanyl, alkoxy, haloalkoxy, alkyl, haloalkyl, amine, and an amine comprising one or more protecting groups (e.g., a protected amine); $R_6$ and $R_7$ are independently selected from the group consisting of hydrogen, hydroxyl, alkoxy, haloalkoxy, halogen, amino, alkyl, and haloalkyl; and $R_8$, $R_9$, $R_{10}$, and $R_{11}$ are independently selected from the group consisting of hydrogen, carbamate, cyclic carbamate, amide, cyclic amide, and a nitrogen-protecting group. Furthermore, in some embodiments, $R_{12}$ is a phenyl ring or a heterocyclic ring comprising hydrogen, hydroxyl, alkyl, halogen, alkoxy, carbonyl, cyano, and/or a nitro group. Some embodiments, moreover, comprise a $^{18}$F-labeled phenethylguanidine wherein $R_{12}$ comprises a solid-support bound linker, e.g., Linker of Solid Support-$R_{12}$—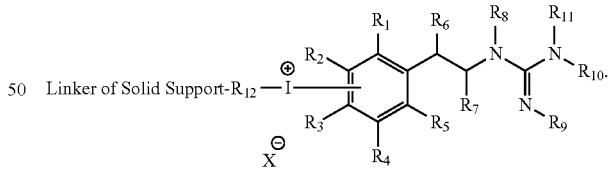

In some embodiments, the [$^{18}$F] fluoride ion source is a no-carrier-added [$^{18}$F] fluoride ion source. For example, in some embodiments, the no-carrier-added [$^{18}$F] fluoride ion source is selected from the group consisting of potassium fluoride/Kryptofix[2,2,2], cesium fluoride, tetraalkylammonium fluoride, and a solid phase fluoride. In some embodiments, $X^-$ is a counter ion selected from the group consisting of halide, sulfate, formate, bromate, tosylate, trifluoracetate, triflate, mesylate, hexaflate, acetate, ascorbate, benzoate, and phosphate. Compositions are also provided that furthermore comprise a free radical scavenger, e.g., as a component of a reaction in which the compositions and compounds according to the technology are made. Examples of free radical scavengers include, in some embodiments, 2,2,6,6-tetramethylpiperidine-N-oxide, 4-aminobenzoic acid, 1,1-diphenylethylene, galvinoxyl, gentisic acid, hydroquinone, thiophenol, DL-alpha-tocopherol, and 2,6-di-tert-butyl-4-methylphenol (BHT). In some embodiments, the compositions provided further comprise water. In some embodiments, a reaction is heated, e.g., in some embodiments, compositions are produced according to a method that comprises heating or microwave irradiation of a reaction vessel holding the iodonium salt and the [$^{18}$F] fluoride ion source.

In another aspect, the technology relates to compositions comprising an $^{18}$F-labeled phenethylguanidine, wherein the $^{18}$F-labeled phenethylguanidine is produced by a method comprising radiofluorinating an iodonium salt of phenethylamine with a [$^{18}$F] fluoride ion source to produce an [$^{18}$F]-labeled phenethylamine; and coupling the [$^{18}$F]-labeled phenethylamine with a guanidinating reagent to produce a [$^{18}$F]-labeled phenethylguanidine, e.g., as described by Reaction 2:

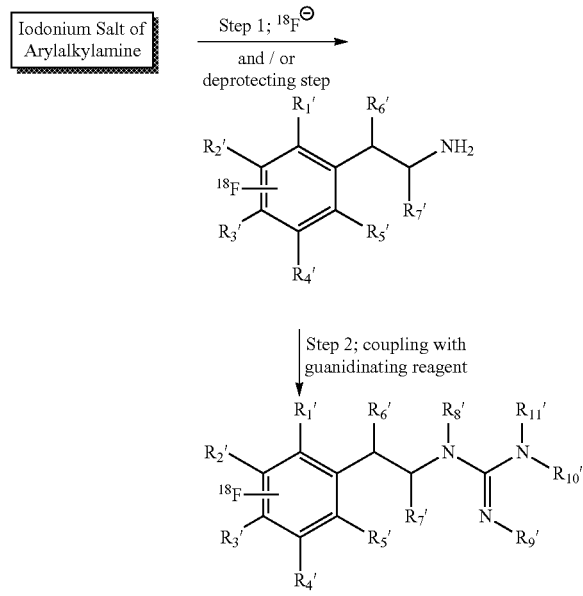

For example, in some embodiments, the iodonium salt of phenethylamine is

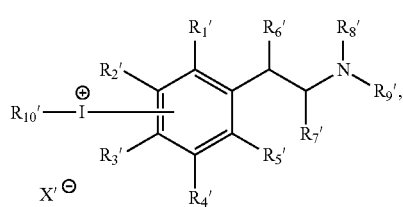

or a salt, free base, or combination thereof, wherein $R_1'$, $R_2'$, $R_3'$, $R_4'$, and $R_5'$ are independently selected from the group consisting of $R_{10}'$—I, hydrogen, halogen, hydroxyl, guanyl, alkoxy, haloalkoxy, alkyl, haloalkyl, amine, and an amine comprising one or more protecting groups (e.g., a protected amine); $R_6'$ and $R_7'$ are independently selected from the group consisting of hydrogen, hydroxyl, alkoxy, haloalkoxy, halogen, amino, alkyl, and haloalkyl; and $R_8'$ and $R_9'$ are independently selected the group from consisting of hydrogen, carbamate, cyclic carbamate, amide, cyclic amide, and nitrogen-protecting group.

The technology is not limited in the guanidinating agent that can be used; for example, in some embodiments, the guanidinating reagent is selected from the group consisting of a cyamide, cyanobromide/ammonia, an S-alkylisothiouronium salt, a carboimide, a chloroformamidine, a dichloroisocyanide, an aminoimnomethanesulfonic acid, O-methylisourea hydrogen sulfate, 1H-pyrazole-1-carboxamidine hydrochloride, benzotriazole-1-carboxamidinium tosylate, 1H-pyrazole-1-[N, N'-Bis(tert-butoxy/benzyloxycarbonyl)]-carboxamidine, N,N'-bis(tert-butoxy/benzyloxycarbonyl)-N''-trifly guanidine, N,N'-bis(tert-butoxy/benzyloxycarbonyl)-2-methyl-2-thiopseudourea, N,N'-bis(tert-butoxy/benzyloxycarbonyl)-thiourea, N,N'-bis(tert-butoxy/benzyloxycarbonyl)-carboimide, and N,N'-bis(tert-butoxy/benzyloxycarbonyl)-1H-benzotriazole-1-carboxamidine.

Embodiments of compositions are provided wherein $R_{10}'$ is a phenyl ring or a heterocyclic ring comprising a hydrogen, hydroxyl, alkyl, halogen, alkoxy, carbonyl, cyano, and/or a nitro group. In addition, in some embodiments, $R_{10}'$ comprises a solid support linker, e.g.,

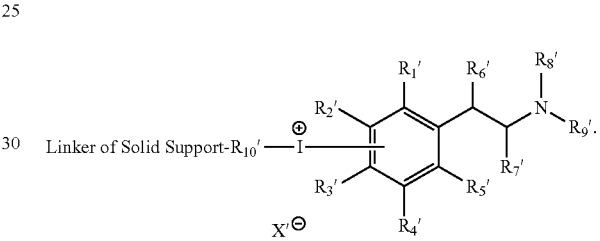

Certain embodiments comprise a composition produced using an iodonium salt of phenethylamine that is an [$^{18}$F]-labeled phenethylamine derivative according to a structure

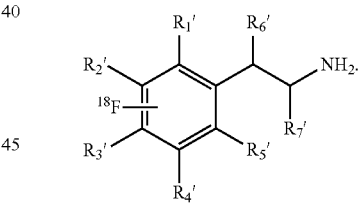

In some embodiments, the [$^{18}$F]-labeled phenethylguanidine has the structure

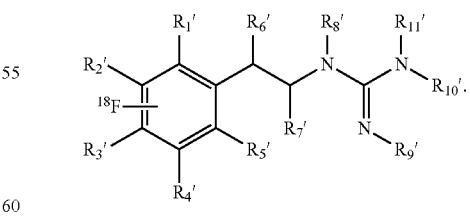

In some embodiments, the [$^{18}$F] fluoride ion source is a no-carrier-added [$^{18}$F] fluoride ion source, e.g., a potassium fluoride/Kryptofix [2,2,2], cesium fluoride, and/or tetraalkylammonium fluoride. In some embodiments, X⁻ is a counter ion selected from the group consisting of halide, sulfate, formate, borate, tosylate, trifluoroacetate, triflate, mesylate, hexaflate, acetate, ascorbate, benzoate, and phosphate. In some embodiments, the compositions comprise a free radical scavenger, e.g., as a component of a reaction to produce embodiments of the technology comprising compositions and compounds. Exemplary free radical scavengers include 2,2,6,6-tetramethylpiperidine-N-oxide, 4-aminobenzoic acid, 1,1-diphenylethylene, galvinoxyl, gentisic acid, hydroquinone, thiophenol, DL-alpha-tocopherol, and 2,6-di-tert-butyl-4-methylphenol (BHT). In some embodiments, the compositions comprise water. In some embodiments, a reaction is heated, e.g., in some embodiments, compositions according to the technology are produced by a method that comprises heating or microwave irradiation of a reaction vessel holding the iodonium salt and the [$^{18}$F] fluoride ion source.

In another aspect, embodiments of the technology comprise compositions wherein the iodonium salt is produced by a method comprising reacting a first compound having the structure

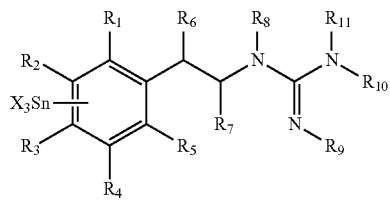

with a second compound that is $R_{12}$-Koser's Reagent, e.g., as described by Reaction 3:

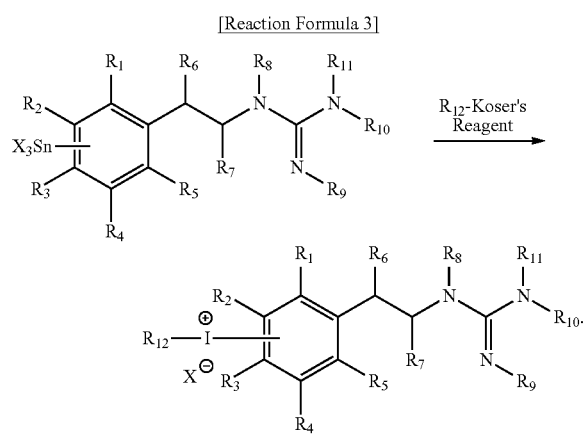

In some embodiments, $R_1$, $R_2$, $R_3$, $R_4$, and $R_5$ are independently selected from the group consisting of $X_3Sn$, hydrogen, halogen, hydroxyl, guanyl, alkoxy, haloalkoxy, alkyl, haloalkyl, amine, and an amine comprising one or more protecting groups (e.g., a protected amine); $R_6$ and $R_7$ are independently selected from the group consisting of hydrogen, hydroxyl, alkoxy, haloalkoxy, halogen, amino, alkyl, and haloalkyl; $R_8$, $R_9$, $R_{10}$, and $R_{11}$ are independently selected the group from hydrogen, carbamate, cyclic carbamate, amide, cyclic amide, and nitrogen-protecting group; and X is an alkyl group. Furthermore, in some embodiments, $R_{12}$ is a phenyl ring or a heterocyclic ring comprising a hydrogen, hydroxyl, alkyl, halogen, alkoxy, carbonyl, cyano, and/or a nitro group.

In another aspect, embodiments comprise compositions (e.g., a reaction pathway intermediate) that are produced by a method comprising reacting a compound having the structure

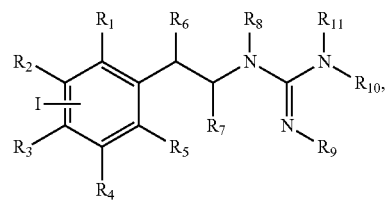

e.g., according to the reaction described by Reaction 4:

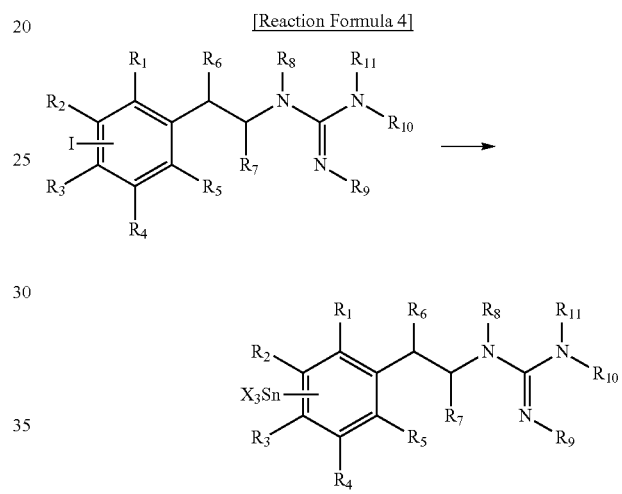

In some embodiments, $R_1$, $R_2$, $R_3$, $R_4$, and $R_5$ are independently selected from the group consisting of halogen (e.g., iodo, bromo), hydrogen, hydroxyl, guanyl, alkoxy, haloalkoxy, alkyl, haloalkyl, amine, and an amine comprising one or more protecting groups (e.g., a protected amine); $R_6$ and $R_7$ are independently selected from the group consisting of hydrogen, hydroxyl, alkoxy, haloalkoxy, halogen, amino, alkyl, and haloalkyl; $R_8$, $R_9$, $R_{10}$, and $R_{11}$ are independently selected the group consisting of hydrogen, carbamate, cyclic carbamate, amide, cyclic amide, and nitrogen-protecting group; and X is an alkyl group.

In another aspect, the iodonium salt of phenethylamine is produced by a method comprising reacting a first compound having the structure

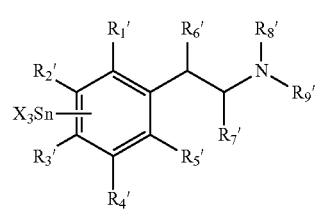

with a second compound that is $R_{10}$'-Koser's Reagent, e.g., according to a reaction described in Reaction 5:

[Reaction Formula 5]

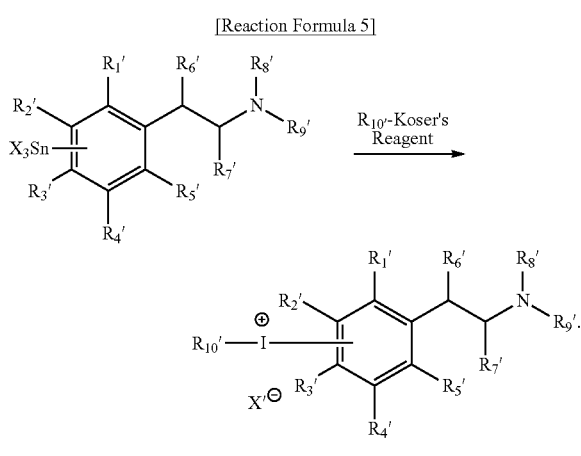

Furthermore, in some embodiments, $R_1'$, $R_2'$, $R_3'$, $R_4'$, and $R_5'$ are independently selected from the group consisting of $X_3Sn$, hydrogen, halogen, hydroxyl, guanyl, alkoxy, haloalkoxy, alkyl, haloalkyl, amine, and an amine comprising one or more protecting groups (e.g., a protected amine); $R_6'$ and $R_7'$ are independently selected from the group consisting of hydrogen, hydroxyl, alkoxy, haloalkoxy, halogen, amino, alkyl, and haloalkyl; $R_8'$ and $R_9'$ are independently selected the group from hydrogen, carbamate, cyclic carbamate, amide, cyclic amide, and nitrogen-protecting group; and X is an alkyl group. In some embodiments, $R_{10}'$ is a phenyl ring or a heterocyclic ring comprising hydrogen, hydroxyl, alkyl, halogen, alkoxy, carbonyl, cyano, and/or a nitro group.

Some aspects of the technology are related to embodiments of compositions wherein a compound is produced by a method comprising reacting a compound having the structure

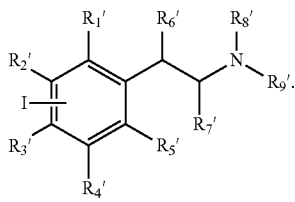

In some embodiments, $R_1'$, $R_2'$, $R_3'$, $R_4'$, and $R_5'$ are independently selected from the group consisting of iodo, bromo, hydrogen, halogen, hydroxyl, guanyl, alkoxy, haloalkoxy, alkyl, haloalkyl, amine, and an amine comprising one or more protecting groups (e.g., a protected amine); $R_6'$ and $R_7'$ are independently selected from the group consisting of hydrogen, hydroxyl, alkoxy, haloalkoxy, halogen, amino, alkyl, and haloalkyl; $R_8'$ and $R_9'$ are independently selected from the group consisting of hydrogen, carbamate, cyclic carbamate, amide, cyclic amide, and nitrogen-protecting group.

The compounds and compositions provided by the technology find use in imaging a tissue, cell, organ, e.g., in a subject. Accordingly, the technology relates, in some embodiments, to methods of imaging comprising contacting a tissue to be imaged with an $^{18}$F-labeled phenethylguanidine, or salt or derivative thereof, and imaging the tissue. In some embodiments, the tissue is selected from the group consisting of heart and adrenal medulla. Furthermore, some embodiments provide that the tissue is suspected of comprising a cancer. In some specific embodiments, the imaging is positron emission tomography (PET).

Furthermore, the technology relates to the use of an $^{18}$F-labeled phenethylguanidine, or salt, free base, or derivative thereof, to image a subject. In additional aspects, the technology relates to embodiments of methods for manufacturing an $^{18}$F-labeled phenethylguanidine having a structure according to

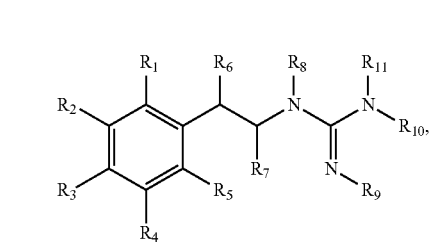

or a salt, a free base, or a combination thereof, comprising radiofluorinating an iodonium salt with an [$^{18}$F] fluoride ion source. In another aspect, the technology relates to embodiments of methods for manufacturing an [$^{18}$F]-labeled phenethylguanidine having a structure according to

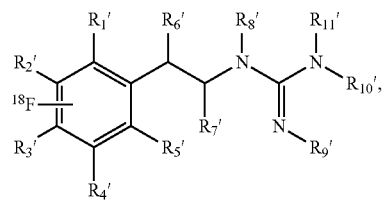

or a salt, a free base, or a combination thereof, comprising the steps of radiofluorinating an iodonium salt of phenethylamine with a [$^{18}$F] fluoride ion source to produce an [$^{18}$F]-labeled phenethylamine; and coupling the [$^{18}$F]-labeled phenethylamine with a guanidinating reagent to produce a [$^{18}$F]-labeled phenethylguanidine. In related embodiments, the technology provides an $^{18}$F-labeled phenethylguanidine, or salt, free base, or derivative thereof, for use as an imaging agent. Moreover, in some embodiments, provided herein is an $^{18}$F-labeled phenethylguanidine, or salt, free base, or derivative thereof, for use as an imaging agent for the diagnosis of cancer or cardiovascular disease.

The labeling technology is not limited to labeled phenethylguanidines. In addition, the technology is applicable to produce $^{18}$F-labeled arylalkylguanidines, $^{18}$F-labeled aryl-Y-alkylguanidines, and/or $^{18}$F-labeled heteroarylalkylguanidines. For example, the technology relates to embodiments of arylalkylguanidine compounds having a general structure:

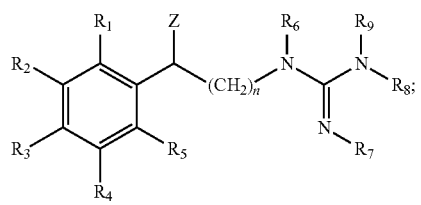

Z = Alkyl or Alkoxy
n = 0 or 2 embodiments of aryl-Y-alkylguanidine compounds having the structure:

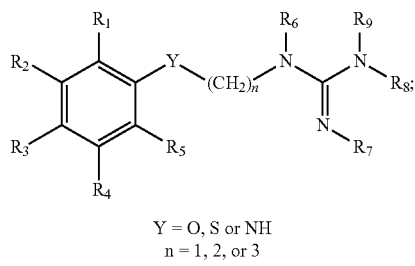

Y = O, S or NH
n = 1, 2, or 3 and embodiments of heteroarylalkylguanidine compounds having the structures:

(H1)
(H2)
(H3)
(H4)

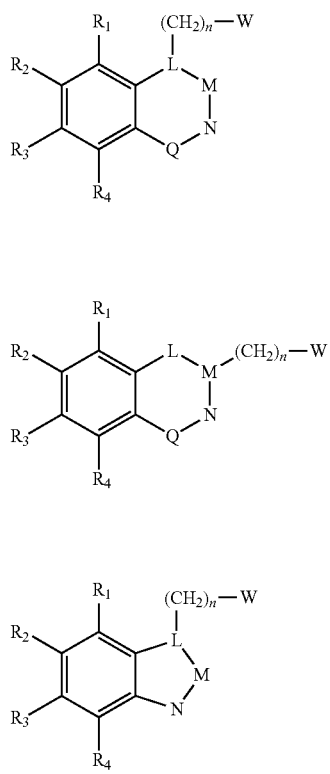

n=0, 1, 2 or 3
L, M, N or Q=$CH_2$, CH, O, N, NH, S, CO, alkyl, haloalkyl, alkoxy, haloalkoxy, $^{18}$F-labeled alkyl or $^{18}$F-labeled alkoxy

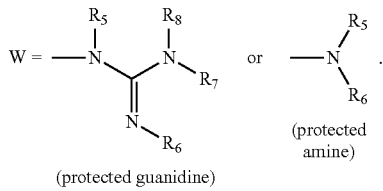

(protected guanidine) (protected amine)

Provided herein are technologies related to methods of producing and/or manufacturing $^{18}$F-labeled arylalkylguanidines, $^{18}$F-labeled aryl-Y-alkylguanidines, and/or $^{18}$F-labeled heteroarylalkylguanidines, e.g., for use as imaging agents, e.g., in PET imaging. For example, some embodiments provide methods in which an $^{18}$F-labeled arylalkylguanidine is produced from an iodonium salt precursor by a single step reaction in solution, e.g.,

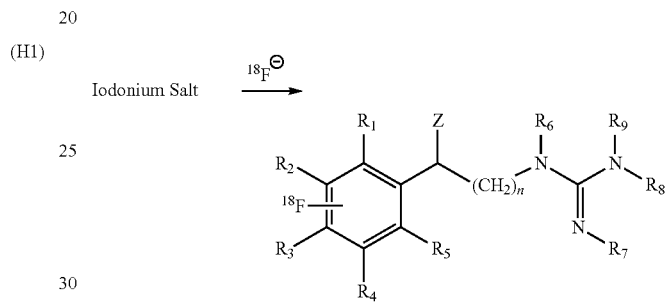

The technology provides related embodiments in which an arylalkylguanidine is produced from an iodonium salt precursor in a single step using a linker, e.g.,

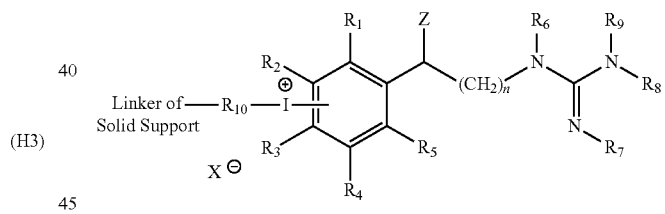

and embodiments in which an arylalkylguanidine is produced from an iodonium salt precursor in solution by the two-step reaction:

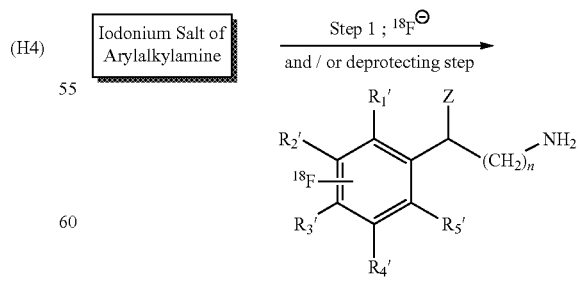

-continued

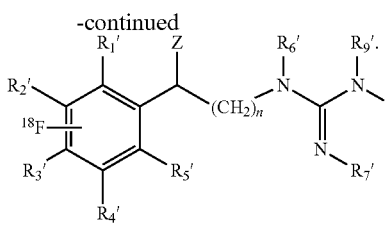

In addition, some embodiments provide methods in which an $^{18}$F-labeled aryl-Y-alkylguanidine is produced from an iodonium salt precursor by a single step reaction in solution, e.g.,

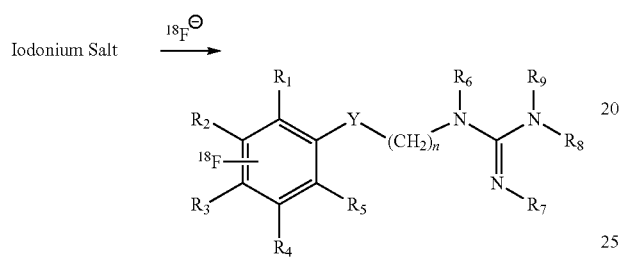

The technology provides related embodiments in which an aryl-Y-alkylguanidine is produced from an iodonium salt precursor in a single step using a linker, e.g.,

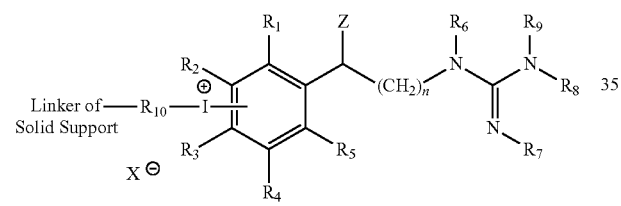

and embodiments in which an aryl-Y-alkylguanidine is produced from an iodonium salt precursor in solution by the two-step reaction:

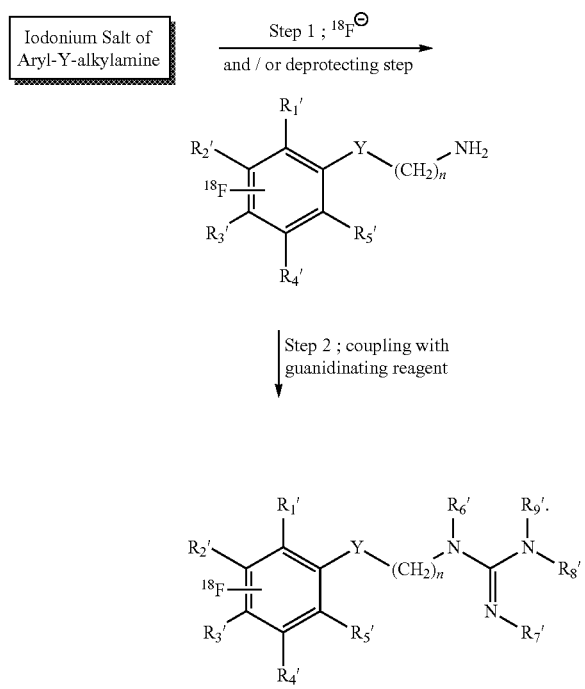

Finally, some embodiments provide methods in which an $^{18}$F-labeled heteroarylalkylguanidine is produced from an iodonium salt precursor by a single step reaction in solution, e.g.,

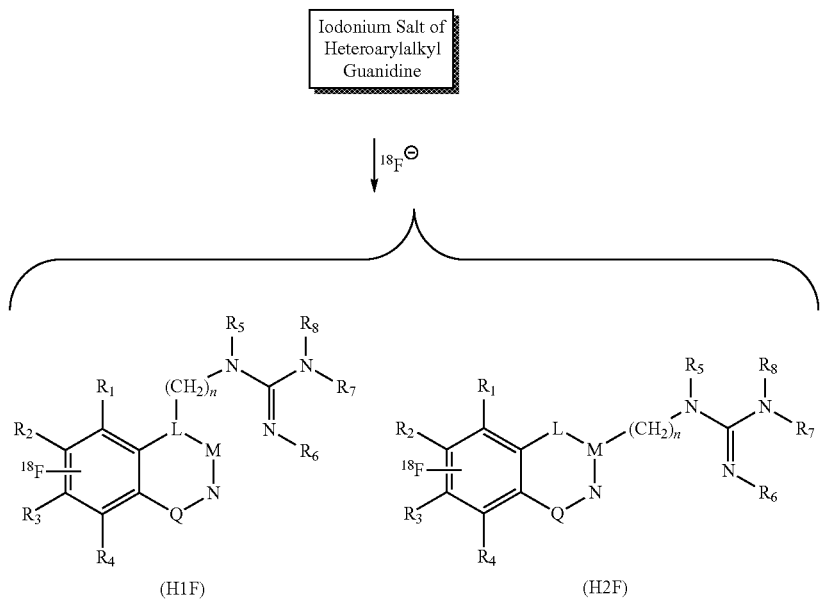

-continued

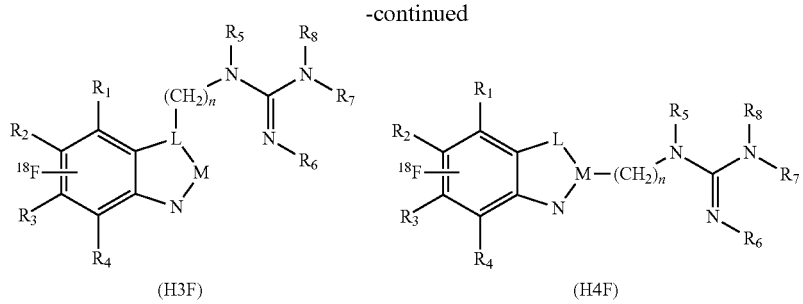

(H3F)    (H4F)

The technology provides related embodiments in which a heteroarylalkylguanidine is produced from an iodonium salt precursor in a single step using a linker, e.g.,

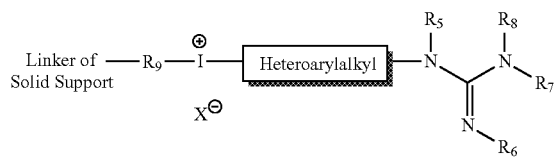

and embodiments in which a heteroarylalkylguanidine is produced from an iodonium salt precursor in solution by the two-step reaction:

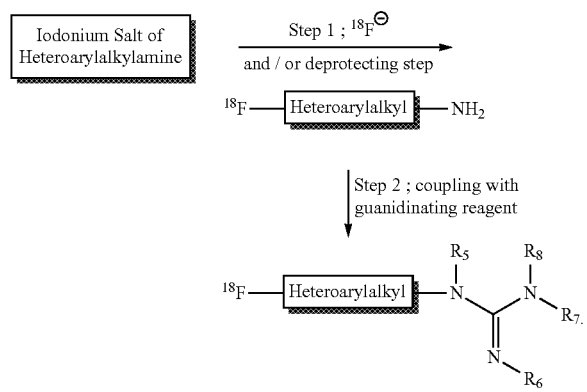

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings:

FIG. 2A and FIG. 2B show two exemplary reaction schemes related to the technology provided herein, e.g., an embodiment for the automated radiosynthesis of 4-[$^{18}$F]fluoro-meta-hydroxyphenethylguanidine ([$^{18}$F]4F-MHPG, compound 1).

FIG. 4A shows a representative HPLC trace for a blood sample drawn at t=2 min after tracer injection. FIG. 4B shows that 100% of the compound was in the sulfur-conjugated form after in vitro incubation of the parent compound with a monkey liver cytosol fraction and 3'-phospho-adenosine-5'phosphosulfate (PAPS).

Figure 1:
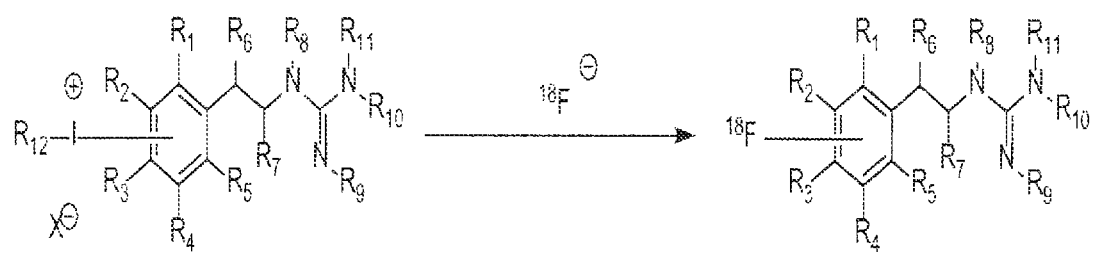
FIG. 1 shows a reaction scheme depicting a radiosynthetic method for preparing $^{18}$F-labeled phenethylguanidines using diaryliodium salt precursors containing a phenethylguanidine moiety.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DETAILED DESCRIPTION

Provided herein is technology related to the preparation of $^{18}$F-labeled phenethylguanidines. In some embodiments, the methods employ a $^{18}$F-labeling step followed by one or two simple steps to yield the final radiolabeled product. It is contemplated that these methods permit automation of the process and thus allow for the routine commercial preparation of the target radiophamaceuticals at central distribution facilities. The radiosynthetic methods provided here (see, e.g., FIGS. 1 & 2) utilize a diaryliodonium salt precursor as a means of incorporating fluorine-18 into the phenyl ring of a phenethylguanidine structure. Embodiments of the methods differ in the specific structures of the side chains of the precursors and of the $^{18}$F-labeled intermediate compounds that are ultimately converted into the target $^{18}$F-phenethylguanidine.

In the description of the technology, the section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

Definitions

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. The term "based on" is not exclusive and allows for being based on additional factors not described, unless the context clearly dictates otherwise. In addition, throughout the specification, the meaning of "a", "an", and "the" include plural references. The meaning of "in" includes "in" and "on."

As used herein the term, "in vitro" refers to an artificial environment and to processes or reactions that occur within an artificial environment. In vitro environments may include, but are not limited to, test tubes and cell cultures. The term "in vivo" refers to the natural environment (e.g., an animal or a cell) and to processes or reactions that occur within a natural environment.

As used herein, the terms "subject" and "patient" refer to any animal, such as a mammal like a dog, cat, bird, livestock, and preferably a human (e.g., a human with a disease such as obesity, diabetes, or insulin resistance).

As used herein, the term "effective amount" refers to the amount of a composition sufficient to effect beneficial or desired results. An effective amount can be administered in one or more administrations, applications, or dosages and is not intended to be limited to a particular formulation or administration route.

As used herein, the term "administration" refers to the act of giving a drug, prodrug, or other agent, or therapeutic treatment to a subject. Exemplary routes of administration to the human body can be through the eyes (ophthalmic), mouth (oral), skin (transdermal, topical), nose (nasal), lungs (inhalant), oral mucosa (buccal), ear, by injection (e.g., intravenously, subcutaneously, intratumorally, intraperitoneally, etc.), and the like.

As used herein, the term "co-administration" refers to the administration of at least two agents or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent.

As used herein, the term "pharmaceutical composition" refers to the combination of an active agent with a carrier, inert or active, making the composition especially suitable for therapeutic use.

The terms "pharmaceutically acceptable" or "pharmacologically acceptable", as used herein, refer to compositions that do not substantially produce adverse reactions, e.g., toxic, allergic, or immunological reactions, when administered to a subject.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present technology.

As used herein, the terms "alkyl" and the prefix "alk-" are inclusive of both straight chain and branched chain saturated or unsaturated groups, and of cyclic groups, e.g., cycloalkyl and cycloalkenyl groups. Unless otherwise specified, acyclic alkyl groups are from 1 to 6 carbons. Cyclic groups can be monocyclic or polycyclic and preferably have from 3 to 8 ring carbon atoms. Exemplary cyclic groups include cyclopropyl, cyclopentyl, cyclohexyl, and adamantyl groups. Alkyl groups may be substituted with one or more substituents or unsubstituted. Exemplary substituents include alkoxy, aryloxy, sulfhydryl, alkylthio, arylthio, halogen, alkylsilyl, hydroxyl, fluoroalkyl, perfluoroalkyl, amino, aminoalkyl, disubstituted amino, quaternary amino, hydroxyalkyl, carboxyalkyl, and carboxyl groups. When the prefix "alk" is used, the number of carbons contained in the alkyl chain is given by the range that directly precedes this term, with the number of carbons contained in the remainder of the group that includes this prefix defined elsewhere herein. For example, the term "$C_1$-$C_4$ alkaryl" exemplifies an aryl group of from 6 to 18 carbons (e.g., see below) attached to an alkyl group of from 1 to 4 carbons.

As used herein, the term "aryl" refers to a carbocyclic aromatic ring or ring system. Unless otherwise specified, aryl groups are from 6 to 18 carbons. Examples of aryl groups include phenyl, naphthyl, biphenyl, fluorenyl, and indenyl groups.

As used herein, the term "heteroaryl" refers to an aromatic ring or ring system that contains at least one ring heteroatom (e.g., O, S, Se, N, or P). Unless otherwise specified, heteroaryl groups are from 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl groups.

As used herein, the term "heterocycle" refers to a non-aromatic ring or ring system that contains at least one ring heteroatom (e.g., O, S, Se, N, or P). Unless otherwise specified, heterocyclic groups are from 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

Aryl, heteroaryl, or heterocyclic groups may be unsubstituted or substituted by one or more substituents selected from the group consisting of $C_{1-6}$ alkyl, hydroxy, halo, nitro, $C_{1-6}$ alkoxy, $C_{1-6}$ alkylthio, trifluoromethyl, $C_{1-6}$ acyl, arylcarbonyl, heteroarylcarbonyl, nitrile, $C_{1-6}$ alkoxycarbonyl, alkaryl (where the alkyl group has from 1 to 4 carbon atoms), and alkheteroaryl (where the alkyl group has from 1 to 4 carbon atoms).

As used herein, the term "alkoxy" refers to a chemical substituent of the formula OR, where R is an alkyl group. By "aryloxy" is meant a chemical substituent of the formula OR', where R' is an aryl group.

As used herein, the term "$C_{x-y}$ alkaryl" refers to a chemical substituent of formula RR', where R is an alkyl group of x to y carbons and R' is an aryl group as defined elsewhere herein.

As used herein, the term "$C_{x-y}$ alkheteraryl" refers to a chemical substituent of formula RR", where R is an alkyl group of x toy carbons and R" is a heteroaryl group as defined elsewhere herein.

As used herein, the term "halide" or "halogen" or "halo" refers to bromine, chlorine, iodine, or fluorine.

As used herein, the term "non-vicinal O, S, or N" refers to an oxygen, sulfur, or nitrogen heteroatom substituent in a linkage, where the heteroatom substituent does not form a bond to a saturated carbon that is bonded to another heteroatom.

As used herein, the group "$R_n$—I" or "R—I" represents a group wherein the iodine atom ("I") is bonded to the main structure, unless specified otherwise. The group "$X_3Sn$" represents a group wherein the tin atom ("Sn") is bonded to the main structure, unless specified otherwise.

As used herein, "Koser's reagent" refers to hydroxy (tosyloxy)iodobenzene ("HTIB"; PhI(OTs)OH)), e.g., as described in Koser, et al. (1982) *J. Org. Chem.* 47: 2487.

For structural representations where the chirality of a carbon has been left unspecified it is to be presumed by one skilled in the art that either chiral form of that stereocenter is possible.

Embodiments of the Technology

The present technology provides novel compounds and novel methods for producing compounds that find use as imaging agents within nuclear medicine applications (e.g., PET imaging and SPECT imaging). The present technology also provides methods for producing imaging compositions for use within nuclear medicine applications. Exemplary compounds and methods of the present technology are described in more detail in the following sections.

I. Radiotracing Agents

Nuclear Radiology is a sub-specialty of Radiology in which radiotracing agents (e.g., compounds containing radioactive forms of atoms) are introduced into the body for the purpose of imaging, evaluating organ function, or localizing disease or tumors. Radiolabelled compounds are used, for example, for both tumor detection and tumor therapy. Many tumor cells have a higher density of cell receptors for various circulating compounds than do non-tumor cells; e.g., endocrine tumors show a high density of cell surface receptors for somatostatin and brain gliomas show a high density of receptors for epidermal growth factor. Thus, a radiolabeled compound that binds to these cellular receptors preferentially binds to the tumor cells. Additionally, angiogenesis, the formation of new blood vessels from established microvasculature, is a critical process for tumor growth. Primary tumors and metastases will not grow beyond 2 mm in diameter without an enhanced vascular supply. Angiogenic cells also have a higher density of cell receptors for various circulating compounds than do non-angiogenic vascular tissue; e.g., receptors for both somatostatin and vascular endothelial growth factor are higher in angiogenic tissue. Thus, a tumor can also be detected by radiolabeled compounds binding to the angiogenic cells that are closely associated with the tumor cells.

The present technology provides new compounds and new methods of producing compounds useful as radiotracing agents. In preferred embodiments, the compounds are structurally related to meta-iodobenzylguanidine (MIBG) and possess kinetic properties superior to MIBG for nuclear medicine applications. In particular, the radiotracing agents of the present technology provide a slower cellular uptake rate and a longer cellular retention length. In preferred embodiments, the present technology provides radiolabeled phenethylguanidines, arylalkylguanidines, aryl-Y-alkyl-guanidines, and heteroarylalkylguanidines. These compounds can be radiolabeled with several radioisotopes, including, but not limited to, radio-halogens such as iodine-123 ($^{123}$I) for single photon imaging (e.g., SPECT imaging), iodine-131 ($^{131}$I) for radiotherapy of adrenergic tumors, and carbon-11 ($^{11}$C) or fluorine-18 ($^{18}$F) for positron emission tomography imaging (e.g., PET imaging). The technology is particularly applicable to $^{18}$F compounds.

Phenethylguanidines differ from benzylguanidines in that they have an additional carbon atom in the side chain of the molecule. The two-carbon side chain structure of phenethylguanidines is similar to that of norepinephrine (NE), the endogenous neurotransmitter of sympathetic neurons in the heart:

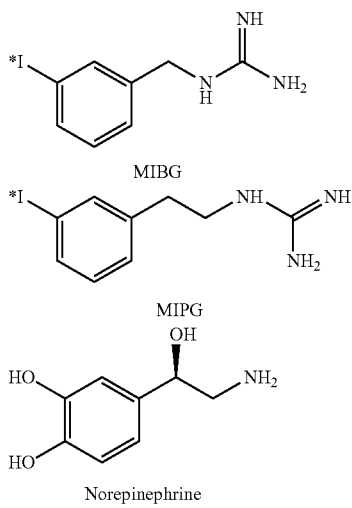

MIBG

MIPG

Norepinephrine

Additional exemplary compounds related to the technology include, but are not limited to, (−)-beta-hydroxyphenethylguanidine, para-methoxy-phenethylguanidine, meta-hydroxyphenethylguanidine, para-hydroxyphenethylguanidine, 3,4-dihydroxyphenethylguanidine, "N-guanyl-meta-octopamine", "N guanyl-norepinephrine", "N-guanyl-(−)-metaraminol", meta-fluorophenethylguanidine, para-fluorophenethylguanidine, ortho-fluorophenethylguanidine, para-fluoro-meta-hydroxy-phenethylguanidine, ortho-fluoro-meta-hydroxy-phenethylguanidine, meta-iodophenethylguanidine, and para-hydroxy-meta-iodo-phenethylguanidine. In preferred embodiments, the compounds of the present technology are radio-labeled (e.g., $^{11}C$, $^{14}C$, $^{18}F$, $^{131}I$ and $^{123}I$).

In preferred embodiments, the compounds of the present technology are described by the following chemical formula:

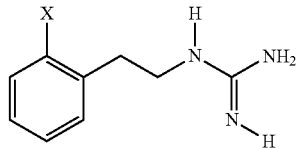

wherein $R_1$, $R_2$, $R_3$, $R_4$ and $R_5$ are the same or different and are independently selected from the group consisting of H, halogen, hydroxyl, guanyl, methoxy, methyl, amino, and nitro, wherein $R_6$ is selected from the group consisting of H and hydroxyl, and wherein $R_7$ is H or $CH_3$. In preferred embodiments, the compound is selected from the group consisting of [$^{11}C$](−)-beta-hydroxyphenethylguanidine, [$^{11}C$]para-methoxy-phenethylguanidine, [$^{11}C$]meta-hydroxyphenethylguanidine, [$^{11}C$]para-hydroxyphenethylguanidine, [$^{11}C$]3,4-dihydroxyphenethylguanidine, "N-[$^{11}C$]guanyl-meta-octopamine", "N-[$^{11}C$]guanyl-norepinephrine", "N-[$^{11}C$]guanyl-(−)-metaraminol", [$^{11}C$]meta-fluorophenethylguanidine, [$^{11}C$]para-fluorophenethylguanidine, [$^{11}C$]ortho-fluorophenethylguanidine, [$^{11}C$]para-fluoro-meta-hydroxyphenethylguanidine, [$^{11}C$]ortho-fluoro-meta-hydroxyphenethylguanidine, [$^{11}C$]meta-iodophenethylguanidine, and [$^{11}C$]para-hydroxy-meta-iodo-phenethylguanidine. In preferred embodiments, the halogen is selected from the group consisting of $^{18}F$, $^{211}At$, $^{76}Br$, $^{131}I$, and $^{123}I$.

Additional exemplary embodiments include, but are not limited to, methods of producing compounds such as the following:

(1) [$^{18}F$], [$^{76}Br$], [$^{211}At$], [$^{131}I$] or [$^{123}I$]-Phenethylguanidines

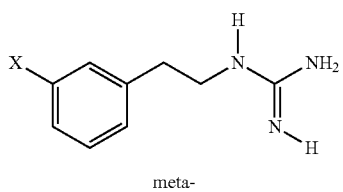

ortho-

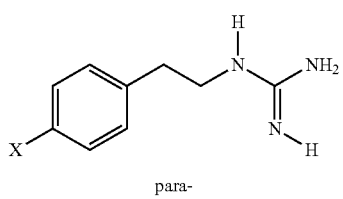

meta-

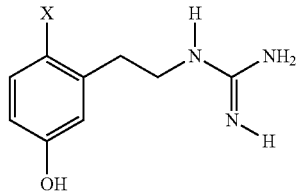

para-

X = [$^{18}F$], [$^{76}Br$], [$^{211}At$], [$^{131}I$] or [$^{123}I$]

(2) [$^{18}F$], [$^{76}Br$], [$^{211}At$], [$^{131}I$] or [$^{123}I$]-Hydroxyphenethylguanidines

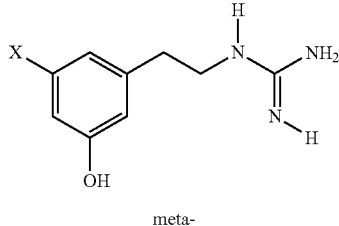

ortho-

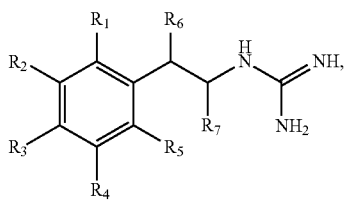

meta-

-continued

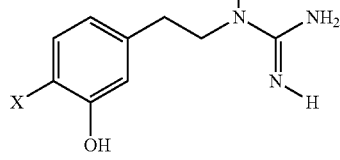

para-

X = [$^{18}$F], [$^{76}$Br], [$^{211}$At], [$^{131}$I] or [$^{123}$I]

(3) [$^{18}$F] or [$^{76}$Br]-Dihydroxyphenethylguanidines

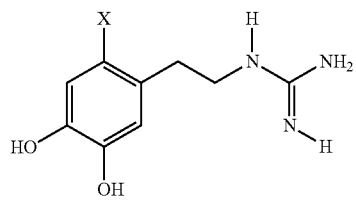

X = [$^{18}$F] or [$^{76}$Br]

(4) [$^{18}$F], [$^{76}$Br], [$^{211}$At], [$^{131}$I] or [$^{123}$I]-β-Hydroxyphenethylguanidines

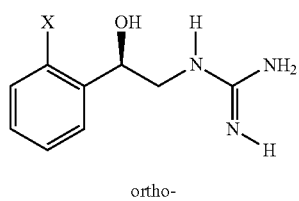

ortho-

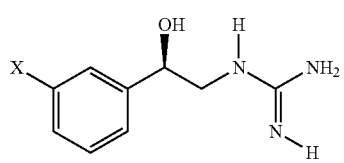

meta-

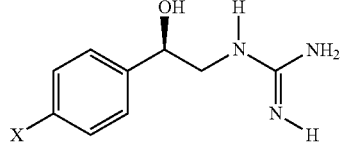

para-

X = [$^{18}$F], [$^{76}$Br], [$^{211}$At], [$^{131}$I] or [$^{123}$I]

(5) [$^{18}$F], [$^{76}$Br], [$^{211}$At], [$^{131}$I] or [$^{123}$I]-3-Hydroxy-β-hydroxyphenethylguanidines

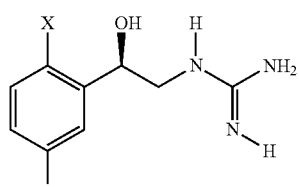

ortho-

-continued

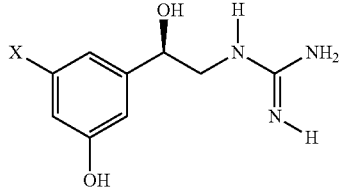

meta-

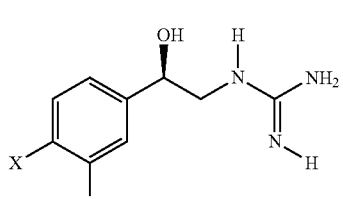

para-

X = [$^{18}$F], [$^{76}$Br], [$^{211}$At], [$^{131}$I] or [$^{123}$I]

In some embodiments, the invention includes methods and compounds related to arylalkylguanidines, aryl-Y-alkylguanidines, and heteroarylalkylguanidines. Arylalkylguanidines are generally described by the following formula:

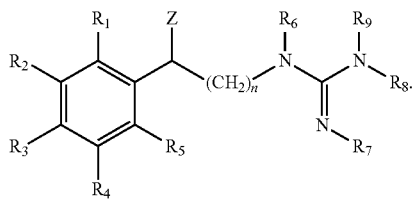

Z = Alkyl or Alkoxy
n = 0 or 2

In some embodiments, $^{18}$F is added to an arylalkylguanidine compound. One compound resulting from such fluorinations is as follows:

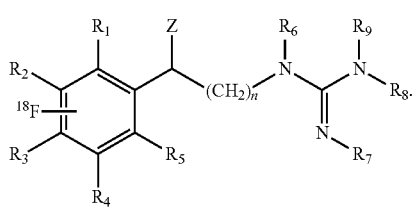

Aryl-Y-alkylguanidines are generally described by the following formula:

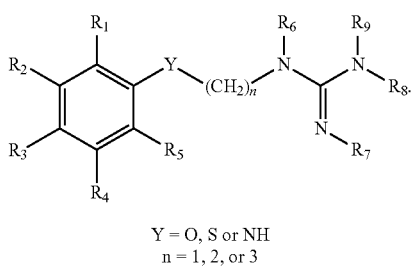

Y = O, S or NH
n = 1, 2, or 3

In some embodiments, $^{18}$F is added to an aryl-Y-alkyl-guanidine compound. One compound resulting from such fluorinations is as follows:

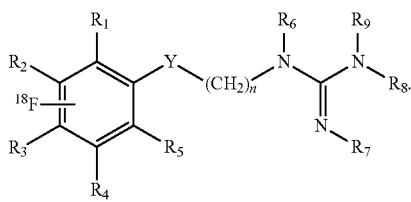

Heteroarylalkylguanidines are generally described by the following formulae:

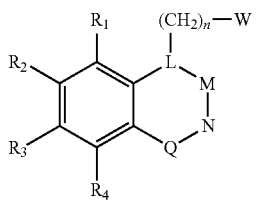
(H1)

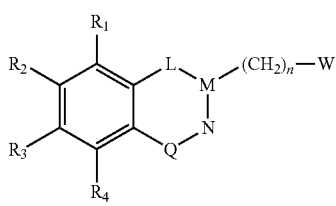
(H2)

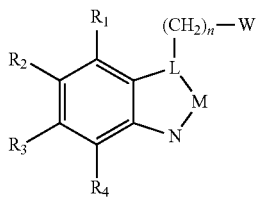
(H3)

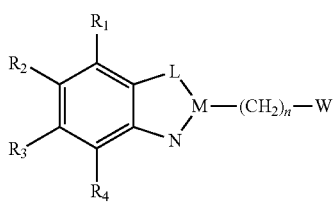
(H4)

n=0, 1, 2 or 3
L, M, N or Q=CH$_2$, CH, O, N, NH, S, CO, alkyl, haloalkyl, alkoxy, haloalkoxy, $^{18}$F-labeled alkyl or $^{18}$F-labeled alkoxy

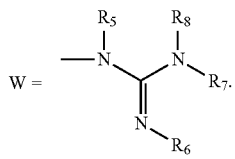

(protected guanidine)

In some embodiments, $^{18}$F is added to an heteroarylalkylguanidine compound. Exemplar compounds resulting from such fluorinations are as follows:

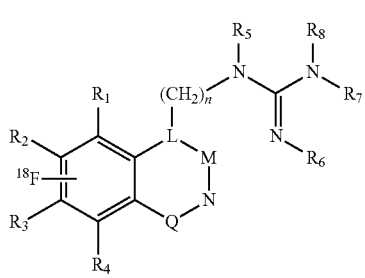
(H1F)

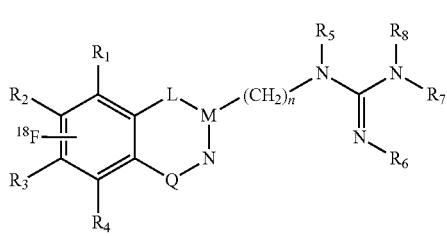
(H2F)

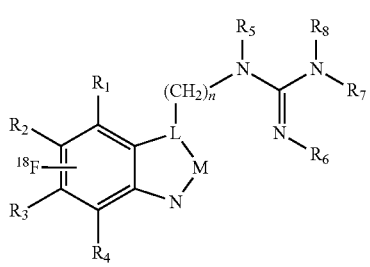
(H3F)

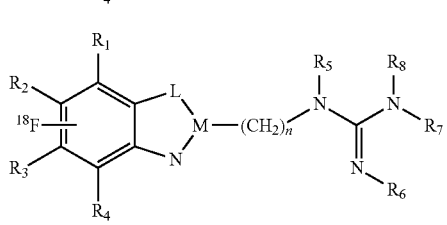
(H4F)

II. Uses Of Radiotracing Agents

The radiotracing agents of the present technology find many uses. In particular, the radiotracing agents of the present technology find use as imaging agents within nuclear medicine imaging protocols (e.g., PET imaging, SPECT imaging).

In preferred embodiments, the radiotracing agents of the present technology are useful as imaging agents within PET imaging studies. PET is the study and visualization of human physiology by electronic detection of short-lived positron emitting radiopharmaceuticals. It is a non-invasive technology that quantitatively measures metabolic, biochemical, and functional activity in living tissue.

The PET scan is a vital method of measuring body function and guiding disease treatment. It assesses changes in the function, circulation, and metabolism of body organs. Unlike MRI (Magnetic Resonance Imaging) or CT (Computed Tomography) scans that primarily provide images of organ anatomy, PET measures chemical changes that occur before visible signs of disease are present on CT and MRI images.

PET visualizes behaviors of trace substances within a subject (e.g., a living body) having a radioimaging agent administered therein by detecting a pair of photons occurring as an electron/positron annihilation pair and moving in directions opposite from each other (see, e.g., U.S. Pat. No. 6,674,083, herein incorporated by reference in its entirety). A PET apparatus is equipped with a detecting unit having a number of small-size photon detectors arranged about a measurement space in which the subject is placed. The detecting unit detects frequencies of the generation of photon pairs in the measurement space on the basis of the stored number of coincidence-counting information items, or projection data, and then stores photon pairs occurring as electron/positron annihilation pairs by coincidence counting and reconstructs an image indicative of spatial distributions. The PET apparatus plays an important role in the field of nuclear medicine and the like, whereby biological functions and higher-order functions of brains can be studied by using it. Such PET apparatuses can be roughly classified into two-dimensional PET apparatuses, three-dimensional PET apparatuses, and slice-septa-retractable type three-dimensional PET apparatuses.

In general, a PET detector or camera typically consists of a polygonal or circular ring of radiation detection sensors placed around a patient area (see, e.g., U.S. Pat. No. 6,822,240, herein incorporated by reference in its entirety). Radiation detection begins by injecting isotopes with short half-lives into a patient's body placed within the patient area. The isotopes are absorbed by target areas within the body and emit positrons. In the human body, the positrons annihilate with electrons. As a result thereof, two essentially monoenergetic gamma rays are emitted simultaneously in opposite directions. In most cases the emitted gamma rays leave the body and strike the ring of radiation detectors.

The ring of detectors includes typically an inner ring of scintillation crystals and an outer ring of light detectors, e.g., photomultiplier tubes. The scintillation crystals respond to the incidence of gamma rays by emitting a flash of light (photon energy), so-called scintillation light, which is then converted into electronic signals by a corresponding adjacent photomultiplier tube. A computer, or similar, records the location of each light flash and then plots the source of radiation within the patient's body by comparing flashes and looking for pairs of flashes that arise simultaneously and from the same positron-electron annihilation point. The recorded data is subsequently translated into a PET image. A PET monitor displays the concentration of isotopes in various colors indicating level of activity. The resulting PET image then indicates a view of neoplasms or tumors existing in the patient's body.

Such detector arrangement is known to have a good energy resolution, but relatively bad spatial and temporal resolutions. Early PET detectors required a single photomultiplier tube to be coupled to each single scintillation crystal, while today, PET detectors allow a single photodetector to serve several crystals, see e.g. U.S. Pat. Nos. 4,864,138; 5,451,789; and 5,453,623, each herein incorporated by reference in their entireties). In such manner the spatial resolution is improved or the number of photodetectors needed may be reduced.

Single Photon Emission Computed Tomography (SPECT) is a tomographic nuclear imaging technique producing cross-sectional images from gamma ray emitting radiopharmaceuticals (single photon emitters or positron emitters). SPECT data are acquired according to the original concept used in tomographic imaging: multiple views of the body part to be imaged are acquired by rotating the camera detector head(s) (e.g., of an Anger camera) around a craniocaudal axis. Using backprojection, cross-sectional images are then computed with the axial field of view (FOV) determined by the axial field of view of the gamma camera. SPECT cameras are either standard gamma cameras that can rotate around the patient's axis or consist of two or even three camera heads to shorten acquisition time. Data acquisition is over at least half a circle)(180°) (used by some for heart imaging), but usually over a full circle. Data reconstruction takes into account the fact that the emitted rays are also attenuated within the patient, e.g., photons emanating from deep inside the patient are considerably attenuated by surrounding tissues. While in CT, absorption is the essence of the imaging process, in SPECT, attenuation degrades the images. Thus, data of the head reconstructed without attenuation correction may show substantial artificial enhancement of the peripheral brain structures relative to the deep ones. The simplest way to deal with this problem is to filter the data before reconstruction. A more elegant but elaborate method used in triple head cameras is to introduce a gamma-ray line source between two camera heads, which are detected by the opposing camera head after being partly absorbed by the patient. This camera head then yields transmission data while the other two collect emission data. Note that the camera collecting transmission data has to be fitted with a converging collimator to admit the appropriate gamma rays.

SPECT is routinely used in clinical studies. For example, SPECT is usually performed with a gamma camera comprising a collimator fixed on a gamma detector that traces a revolution orbit around the patient's body. The gamma rays, emitted by a radioactive tracer accumulated in certain tissues or organs of the patient's body, are sorted by the collimator and recorded by the gamma detector under various angles around the body. From the acquired planar images, the distribution of the activity inside the patient's body is computed using certain reconstruction algorithms. Generally, the so-called Expectation-Maximization of the Maximum-Likelihood (EM-ML) algorithm is used, as described by Shepp et al. (IEEE Trans. Med. Imaging 1982; 2:113-122) and by Lange et al. (J. Comput. Assist. Tomogr. 1984; 8:306-316). This iterative algorithm minimizes the effect of noise in SPECT images.

In preferred embodiments, the radiotracing agents of the present technology are used as imaging agents for PET imaging and SPECT imaging. It is contemplated that the radiotracing agents of the present technology are provided to a nuclear pharmacist or a clinician in kit form.

A pharmaceutical composition produced according to the present technology comprises use of one of the aforementioned radiotracing agents and a carrier such as a physiological buffered saline solution or a physiologically buffered sodium acetate carrier. It is contemplated that the composition will be systemically administered to the patient as by intravenous injection. Suitable dosages for use as a diagnostic imaging agent are, for example, from about 0.2 to about 2.0 mCi of I-131 labeled radiotracing agent for the adrenal medulla or tumors therein, and from about 2.0 to about 10.0 mCi of the I-123 labeled agent for imaging of the heart and adrenal medulla or tumors therein. For use as a therapeutic agent, a higher dosage is required, for example, from about 100 to about 300 mCi of the radiotracing agent material.

It will be appreciated by those skilled in the art that the imaging agents of the present technology are employed in accordance with conventional methodology in nuclear medicine in a manner analogous to that of the aforementioned radiotracing agents. Thus, a composition of the present technology is typically systemically applied to the patient, and subsequently the uptake of the composition in the selected organ is measured and an image formed, for example, by means of a conventional gamma camera.

Further understanding of use of the present technology can be obtained from the following examples and from Kline, et al.: "Myocardial Imaging in Man with [123 I]-Meta-Iodobenzylguanidine," J. Nucl. Med. 22:129-132, 1981; Wieland, et al: "Myocardial Imaging with a Radioiodinated Norepinephrine Storage Analog," J. Nucl. Med. 22:22-31, 1981; Valk, et al: "Spectrum of Pheochromocytoma in Multiple Endocrine Neoplasia: A Scintigraphic Portrayal Using $^{131}$I-Meta-Iodobenzylguanidine," Ann. Intern. Med., Vol. 94, pp. 762-767 (1981); Sisson, et al.: "Scintigraphic Localization of Pheochromocytoma," New Eng. J. Med., Vol. 305, pp. 12-17, (1981); and Lynn, et al., "Portrayal of Pheochromocytoma and Normal Human Adrenal Medulla by m-[I-123]-iodobenzylguanidine", J. Nucl. Med., Vol. 25, Vol. 436-440 (1984); and U.S. Pat. Nos. 4,584,187 and 4,622,217; these articles are specifically incorporated by reference herein.

III. Methods of Producing 18-F Radiolabeled Phenethylguanidines

To prepare some embodiments of compounds according to the technology described herein, a radiosynthetic scheme was used for preparing [$^{18}$F]4F-MHPG in which an intermediate fluorine-18 labeled compound 4-[$^{18}$F]fluoro-meta-tyramine ([$^{18}$F]4F-MT) was produced using a conventional method for preparing 6-[$^{18}$F]fluoro-dopamine (see, e.g., Ding et al. (1991) "Synthesis of high specific activity 6-[$^{18}$F]fluorodopamine for PET studies of sympathetic nervous tissue", J Med Chem. 34: 861-3) as modified by Langer (see, e.g., Langer et al. (2000) "High specific radioactivity (1R,2S)-4-[$^{18}$F]fluorometaraminol: a PET radiotracer for mapping sympathetic nerves of the heart", Nucl Med Biol. 27: 233-8; Langer et al. (2001) "Synthesis of high-specific-radioactivity 4- and 6-[$^{18}$F]fluorometaraminol-PET tracers for the adrenergic nervous system of the heart", Bioorg Med Chem. 9: 677-94). Then, purified [$^{18}$F]4F-MT was reacted with cyanogen bromide (CNBr) for 3 minutes at 120° C. to prepare the cyanamide intermediate. This was then reacted with NH$_4$Br/NH$_4$OH for 15 minutes at 130° C., followed by HPLC purification, to yield the target compound [$^{18}$F]4F-MHPG. The radiosynthesis was reproducible and the final product was routinely prepared at >95% radiochemical purity. Some steps of this synthesis were performed manually; in addition, the synthesis took approximately 4 hours to complete and the synthesis provided relatively low radiochemical yields and low specific activities. See, e.g., Jang et al (2013) "Synthesis and bioevaluation of [$^{18}$F]4-fluoro-m-hydroxyphenethylguanidine ([$^{18}$F]4F-MHPG): a novel radiotracer for quantitative PET studies of cardiac sympathetic innervation", Bioorg Med Chem Lett. 23: 1612-6.

Conventional reaction schemes, or reaction schemes comprising one or more conventional steps, for producing compounds according to the technology (e.g., a $^{18}$F-labeled phenethylguanidine) were tested and found to be unsatisfactory for automated synthesis, e.g., due to high pressures developed in the reaction vial when heating with NH$_4$Br/NH$_4$OH at 130° C., due to the use of LiAlH$_4$, steps requiring manual steps performed by hand, and/or requiring long reaction and/or work-up times. Thus, alternative approaches were developed for an automated radiosynthesis.

For example, in one embodiment, the methods related to the technology involve using a diaryliodonium salt precursor in which the entire side chain, including the guanidine moiety itself, is unprotected ($R_8$, $R_9$, $R_{10}$, and/or $R_{11}$=hydrogen) or protected (one or more of $R_8$, $R_9$, $R_{10}$, and/or $R_{11}$=N-protecting group), directly yielding a $^{18}$F-labeled phenethylguanidine structure (see FIG. 1). During the development of this technology, a model compound ($R_3$=$R_{12}$—I, $R_1$, $R_2$, $R_4$-$R_{11}$=hydrogen) was tested and found to produce a 7% radiochemical yield in the $^{18}$F-labeling step. Similarly, a second model compound ($R_3$=$R_{12}$—I, $R_1$, $R_2$, $R_4$-$R_7$=hydrogen, $R_8$-$R_{11}$=tert-Boc) was tested. After $^{18}$F-labeling and treatment with mild acid for simple N-Boc deprotection, followed by HPLC purification, this second model compound was found to produce the final target product (4[$^{18}$F]fluoro-phenethylguanidine) at 10% radiochemical yield (end of synthesis).

Figure 2A:
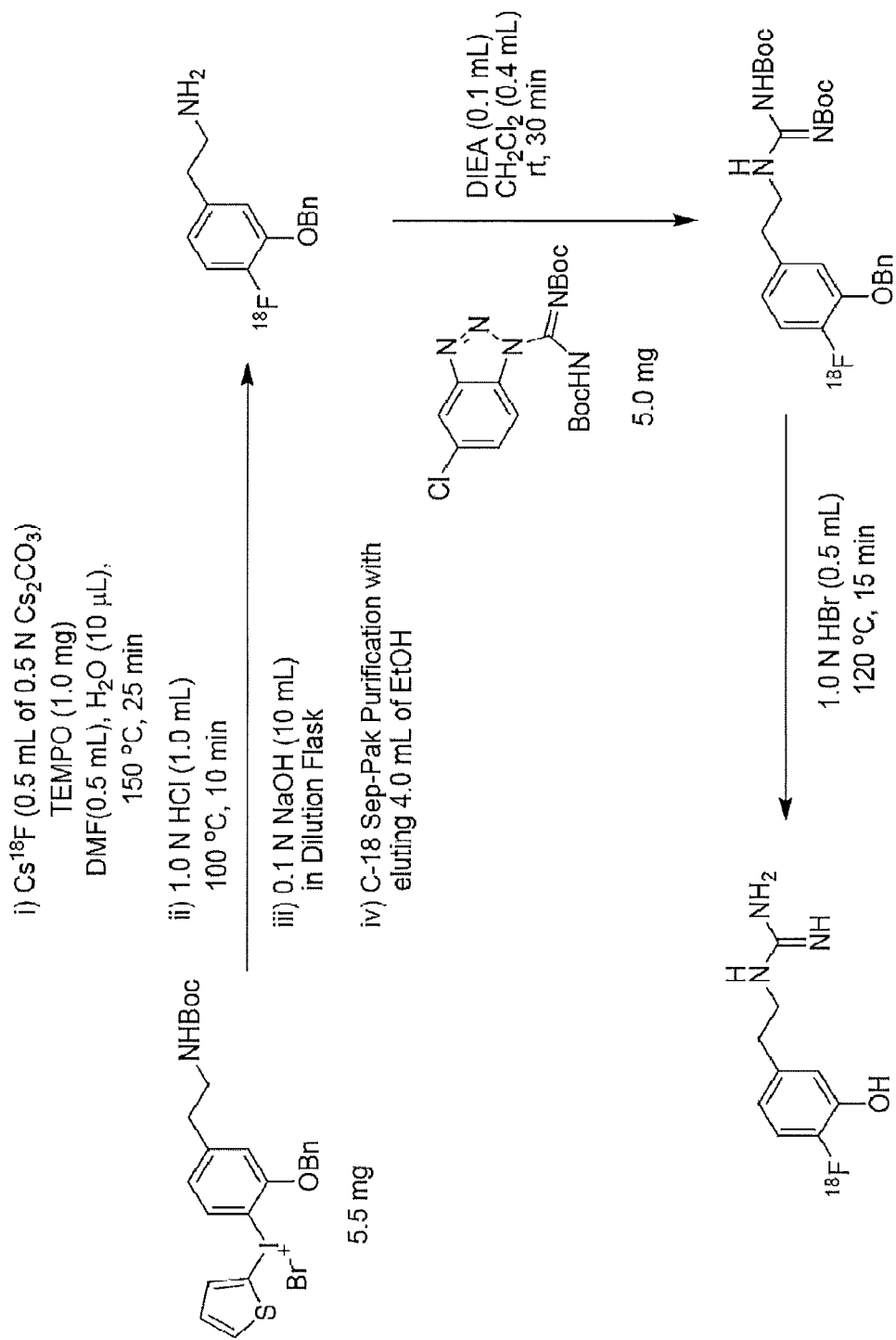
FIGS. 2A and 2B show reaction schemes depicting radiosynthetic methods for preparing 4-[$^{18}$F]fluoro-meta-hydroxyphenethylguanidine using a diaryliodium salt precursor containing a protected phenethylamine moiety. This method can be generalized to prepare many other $^{18}$F-phenethylguanidine structures, such as those described in U.S. Pat. No. 7,534,418.

In another embodiment, the methods relate to a two-step reaction to prepare a $^{18}$F-phenethylguanidine (see FIG. 2A). The $^{18}$F-labeling step uses a diaryliodonium salt precursor with an N-protected phenethylamine moiety instead of the guanidine group used in the first method. The N-Boc-aminoethylphenyl(2-thienyl) iodonium salt provides very high radiochemical yields in the $^{18}$F-labeling step. Treatment with mild acid for simple N-Boc deprotection followed by purification using a C18 Sep-Pak delivers 4-[$^{18}$F]fluoro-meta-tyramine as an intermediate. This is then reacted with a guanylating agent (N,N'-diBoc-5-chlorobenzotriazole) to convert the primary amine into a guanidine. Cleavage of both of the benzyloxy and N-Boc protecting groups with acid in the final step generates the $^{18}$F-labeled phenethylguanidine, e.g., 4-[$^{18}$F]fluoro-meta-hydroxy phenethylguanidine([$^{18}$F]4F-MHPG).

Figure 2B:
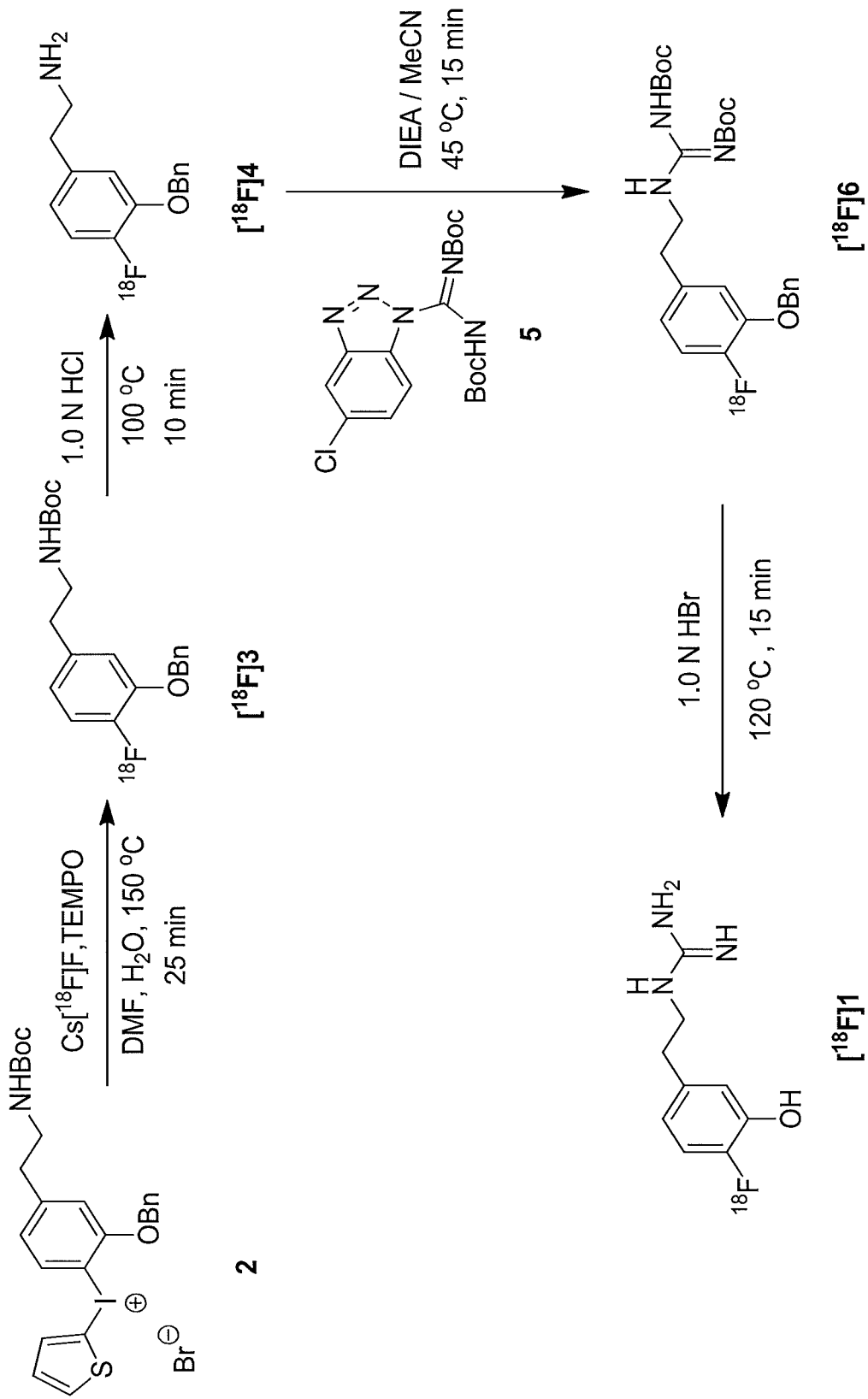

In yet another embodiment, an automated method was developed for the preparation of [$^{18}$F]4F-MHPG (see, e.g., FIG. 2B). In this embodiment, a single $^{18}$F-labeling step is followed by additional steps to yield the final product. In some embodiments, two reaction modules (e.g., GE TRAC-ERlab FX$_{FN}$ modules) (in adjacent hot-cells) were used in sequence for a fully automated synthesis of the [$^{18}$F] compound 1 (FIG. 2B). The first FX$_{FN}$ module was used for production of 3-benzyloxy-4-[$^{18}$F]fluoro-meta-tyramine [$^{18}$F] (FIG. 2B, compound 4), while the second FX$_{FN}$ module was used to convert the [$^{18}$F] compound 4 (FIG. 2B) into the final product 1, as shown in FIG. 2B. In the first step of the reaction, the iodonium salt precursor (FIG. 2B, compound 2) was reacted with Cs[$^{18}$F]F in DMF containing the radical scavenger TEMPO to prepare the [$^{18}$F] compound 3 (FIG. 2B). Removal of the Boc protecting group from 3 using 1.0 N HCl provided the intermediate [$^{18}$F] compound 4. In general, approximately 1.4 Ci of [$^{18}$F]F− was used and 170-250 mCi of [$^{18}$F] compound 4 was obtained with a 15±3% radiochemical yield and >95% radiochemical purity. Compound 4 was purified using a C-18 Sep-Pak cartridge and eluted into the reaction vial of the second FX$_{FN}$ module.

The transferred solution comprising [$^{18}$F] compound 4 (170-250 mCi) was evaporated under a stream of nitrogen and then cooled. A solution of N,N'-bis-(tert-butoxycarbonyl)-5-chloro-1H-benzotriazole-1-carboxamidine (FIG. 2B, compound 5) in a mixed solution of DIEA and MeCN was added to the reactor vessel containing [$^{18}$F] compound 4 and the resulting mixture was heated at 45° C. for 15 minutes to form [$^{18}$F] compound 6 (FIG. 2B). Next, the simultaneous removal of the benzylether protecting group and the N,N'-di-Boc protecting groups was achieved by adding 1.0 N HBr to the reactor vessel and heating at 120° C. for 15 minutes. After cooling, a mixture of 1.0 N NaOH and a buffer solution was added to the reaction vial. The crude product was injected onto a reverse-phase HPLC column (Phenomenex Synergi 10 micron Hydro-RP 80A, 250×10 mm, 5% EtOH in 60 mM NaH$_2$PO$_4$ buffer, flow rate 4.0 mL/min, $\lambda_{224}$ nm) and [$^{18}$F] compound 1 (FIG. 2B) was collected, e.g., at approximately 28-30 minutes. Typically, 55-125 mCi of [$^{18}$F] compound 1 was obtained with a 7±3% overall radiochemical yield and >99% radiochemical purity. The specific activity (SA) averaged 1.2±0.3 Ci/μmol. Total synthesis time from end of bombardment (EOB) was approximately 150 minutes. Some embodiments contemplate similar syntheses on a synthesizer having two reaction vials (e.g., a GE TRACERlab FX N Pro Synthesizer) to perform the synthesis in a single automated radiosynthesis module.

It is contemplated that these methods are used in certain embodiments to produce other $^{18}$F-phenethylguanidine structures such as those provided in U.S. Pat. No. 7,534,418, which is incorporated herein by reference in its entirety for all purposes.

Moreover, based on the simplicity and robust yields of this method, it is contemplated that this second approach is automated in particular embodiments to produce sufficiently large batches of [$^{18}$F]4F-MHPG at high specific activities and high radiochemical yields to prepare and distribute the compounds daily to stand-alone PET centers.

IV. Application of 18F-Labeling Method to Producing Additional Guanidine Imaging Agents In addition to the embodiment of the technology described above for preparing $^{18}$F-labeled phenethylguanidines, the technology comprises embodiments in which the same approach (or similar approaches) is used to prepare other $^{18}$F-labeled guanidine compounds that are useful as PET imaging agents. These include, but are not limited to:
A. $^{18}$F-labeled arylalkylguanidines, including, but not limited to, $^{18}$F-benzylguanidines and $^{18}$F-arylpropylguanidines, such as 4-[$^{18}$F]fluoro-meta-hydroxy-benzylguanidine and 4-[$^{18}$F]fluoro-meta-hydroxy-phenpropylguanidine.
B. $^{18}$F-labeled aryl-Y-alkylguanidines, in which Y is O, S, or NH, such as 4-[$^{18}$F]fluoro-meta-hydroxy-phenoxyethylguanidine.
C. $^{18}$F-labeled heteroarylalkylguanidines, such as 6-[$^{18}$F]fluoro-7-hydroxy-guanoxan.

The $^{18}$F-labeling methodology described above is used in some embodiments to prepare $^{18}$F-labeled benzylguanidines. Embodiments of these methods are distinct from conventional approaches for preparing compounds such as meta-[$^{18}$F]fluoro-benzylguanidine (see, e.g., Garg, et al. (1994) "Synthesis and preliminary evaluation of para- and meta-[$^{18}$F]fluorobenzylguanidine", *Nucl Med Biol* 21: 97-103). It is contemplated that novel imaging agents comprising [$^{18}$F]-labeled arylpropylguanidines are useful PET imaging agents of cardiac sympathetic innervation and adrenergic tumors.

The labeling technology is not limited to particular $^{18}$F-labeled arylalkylguanidines, aryl-Y-alkylguanidines, and/or heteroarylalkylguanidines. For example, the technology relates to embodiments of arylalkylguanidine compounds having a general structure:

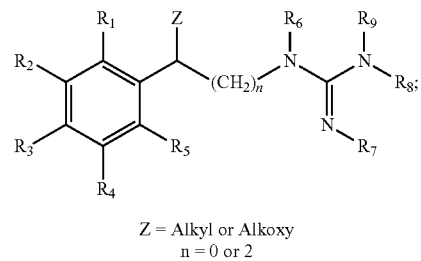

Z = Alkyl or Alkoxy
n = 0 or 2 embodiments of aryl-Y-alkylguanidine compounds having the structure:

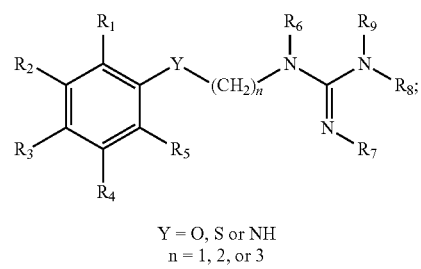

Y = O, S or NH
n = 1, 2, or 3 and embodiments of heteroarylalkylguanidine compounds having the structures:

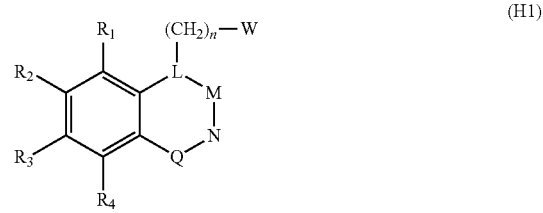

(H1)

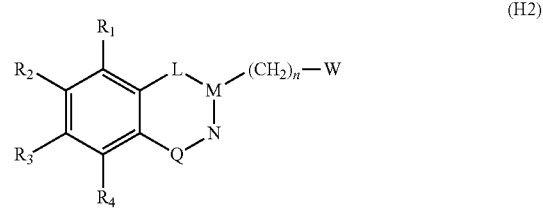

(H2)

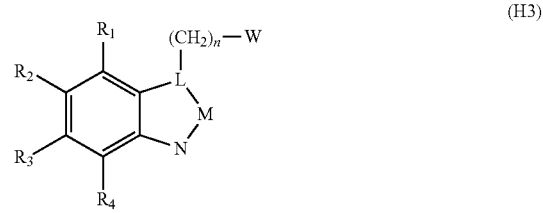

(H3)

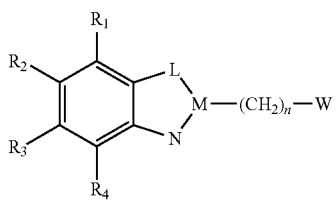

(H4)

n=0, 1, 2 or 3
L, M, N or Q=CH$_2$, CH, O, N, NH, S, CO, alkyl, haloalkyl, alkoxy, haloalkoxy, $^{18}$F-labeled alkyl or $^{18}$F-labeled alkoxy

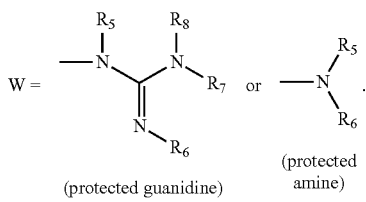

(protected guanidine)   (protected amine)

Provided herein are technologies related to methods of producing and/or manufacturing $^{18}$F-labeled arylalkylguanidines, aryl-Y-alkylguanidines, and/or heteroarylalkylguanidines, e.g., for use as imaging agents, e.g., in PET imaging. For example, some embodiments provide methods in which an $^{18}$F-labeled arylalkylguanidine is produced from an iodonium salt precursor by a single step reaction in solution, e.g.,

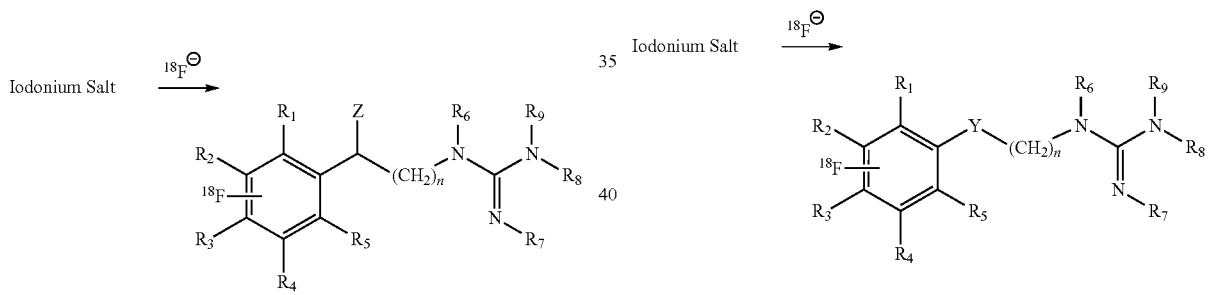

The technology provides related embodiments in which an arylalkylguanidine is produced from an iodonium salt precursor in a single step using a linker, e.g.,

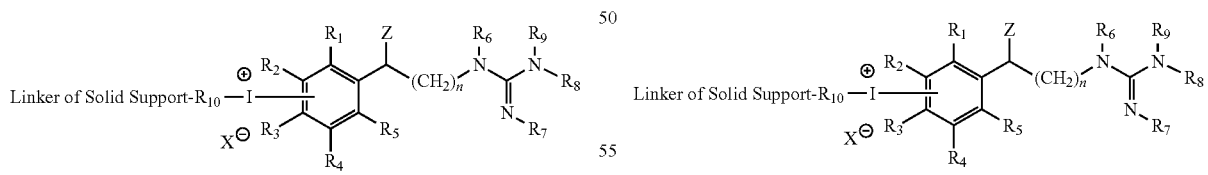

(wherein in this and other structures X$^-$ is a counterion) and embodiments in which an arylalkylguanidine is produced from an iodonium salt precursor in solution by the two-step reaction:

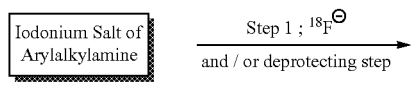

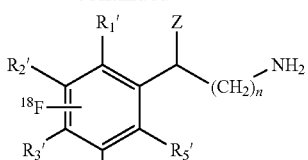

Step 2 ; coupling with guanidinating reagent

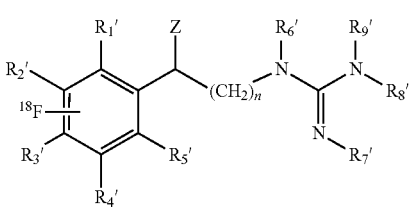

In addition, some embodiments provide methods in which an $^{18}$F-labeled aryl-Y-alkylguanidine is produced from an iodonium salt precursor by a single step reaction in solution, e.g.,

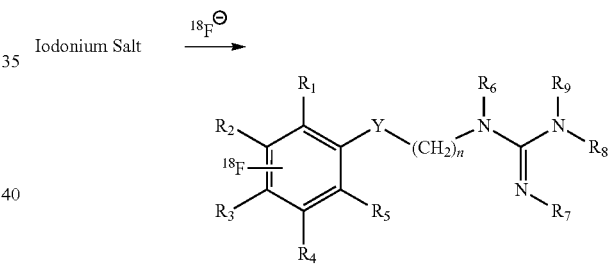

The technology provides related embodiments in which an aryl-Y-alkylguanidine is produced from an iodonium salt precursor in a single step using a linker, e.g.,

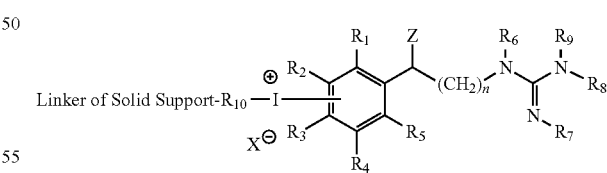

and embodiments in which an aryl-Y-alkylguanidine is produced from an iodonium salt precursor in solution by the two-step reaction:

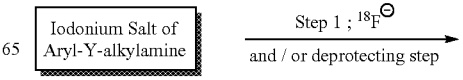

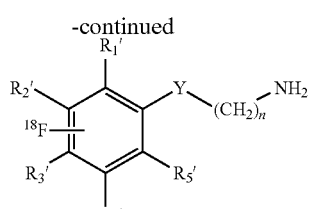

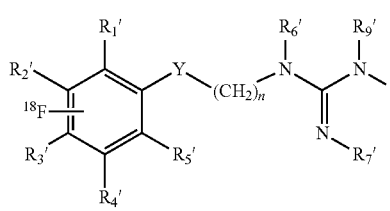

Finally, some embodiments provide methods in which an $^{18}$F-labeled heteroarylalkylguanidine is produced from an iodonium salt precursor by a single step reaction in solution, e.g.,

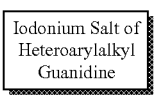

The technology provides related embodiments in which a heteroarylalkylguanidine is produced from an iodonium salt precursor in a single step using a linker, e.g.,

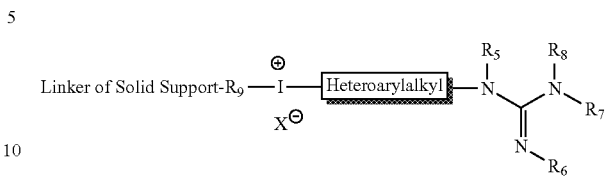

and embodiments in which a heteroarylalkylguanidine is produced from an iodonium salt precursor in solution by the two-step reaction:

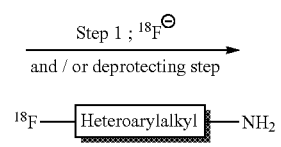

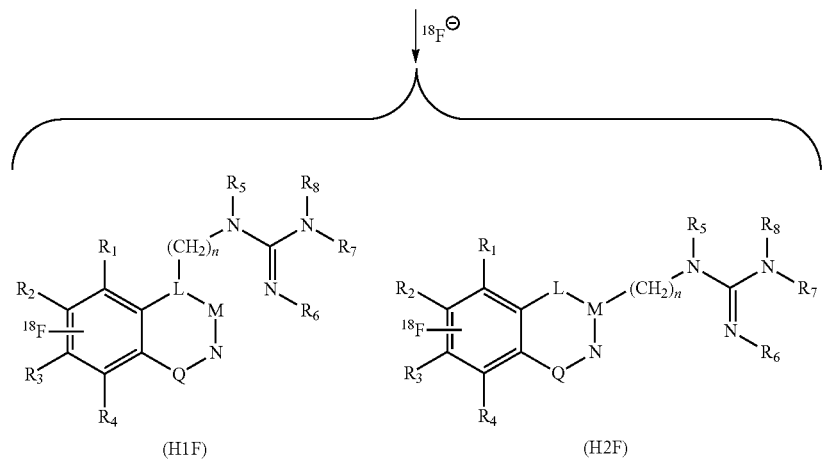

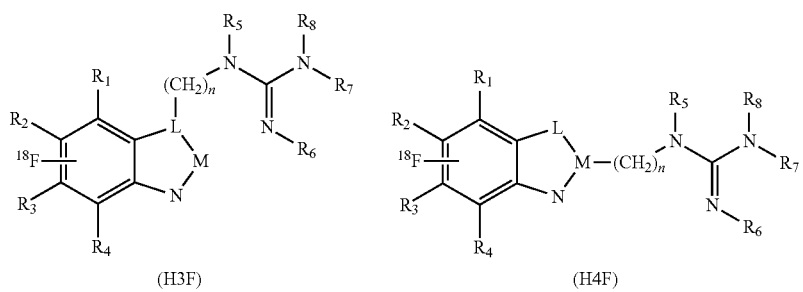

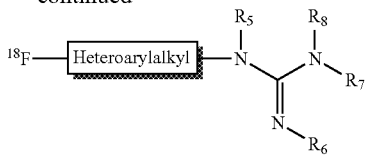

Example 2 demonstrates that compositions comprising $^{18}$F-labeled aryl-Y-alkylguanidine compounds are successful as PET imaging agents. These results are based on evaluating $^{11}$C-labeled analogs of phenoxyethylguanidine as potential imaging agents for cardiac sympathetic innervation and adrenergic tumors in an isolated rat heart system.

Figure 14:
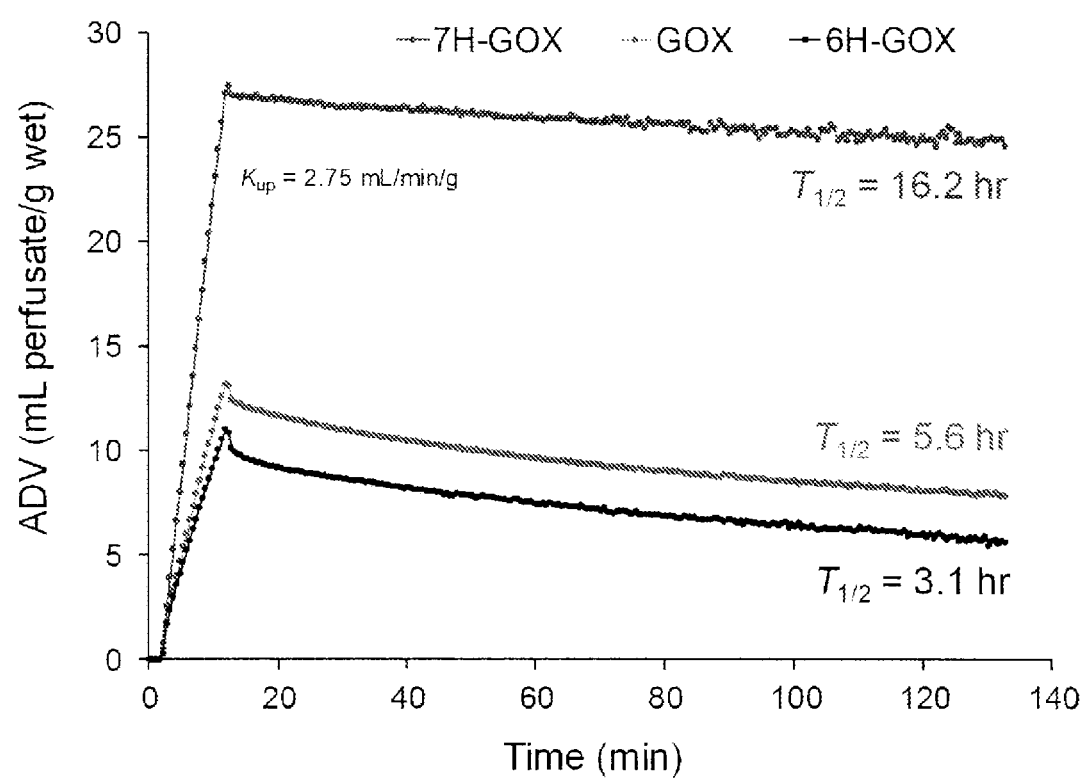
FIG. 14 is a plot showing the kinetics of $^{11}$C-guanoxan (GOX) and two ring-hydroxylated analogs, $^{11}$C-7-hydroxy-guanoxan (7H-GOX) and $^{11}$C-6-hydroxy-guanoxan (6H-GOX).

Heterocyclic compounds with side chains terminating with a guanidine group are good substrates of the norepinephrine transporter (NET) and have pharmacological activity in cardiac sympathetic innervation. See, e.g., Broadley K J. *Autonomic Pharmacology*. London: Taylor & Francis (1996). For example, the heteroarylalkylguanidine compound 2-(2,3-dihydro-1,4-benzodioxin-2-ylmethyl) guanidine, which is known as "guanoxan" has pharmacological activity, in particular, guanoxan exhibits "sympatholytic" activity that prevents the release of norepinephrine from nerve terminals. Example 3 shows that a guanoxan compound is useful as an imaging agent. As shown in FIG. 14, ring-hydroxylated analogs of guanoxan showed favorable uptake and retention time. As such, these data show that an $^{18}$F-labeled analog of a ring hydroxylated analog of guanoxan, (e.g., 6-[$^{18}$F]fluoro-7-hydroxy-guanoxan) is useful as an imaging agent, for example to image adrenergic tumors and cardiac sympathetic innervation.

In summary, in addition to the technology related to the $^{18}$F-labeling method for preparing ring $^{18}$F-fluorinated phenethylguanidines for PET imaging, the technology provided herein finds use to synthesize several other classes of guanidine compounds with a ring $^{18}$F-fluorine moiety. For example, as shown by the examples and as discussed herein, several classes of imaging agents with structural similarity to phenethylguanidines (e.g., arylalkylguanidines, aryl-Y-alkylguanidines, and heteroarylalkylguanidines) were evaluated and the results demonstrate that these additional agents share a unified clinical application with $^{18}$F-labeled phenethylguanidines as imaging agents. The specific imaging targets of these imaging agents include, but are not limited to, the sympathetic innervation of the heart and other organs, the adrenal medulla, and neuroendocrine tumors such as neuroblastoma and pheochromocytoma.

Although the disclosure herein refers to certain illustrated embodiments, it is to be understood that these embodiments are presented by way of example and not by way of limitation.

EXAMPLES

Example 1

Biological Evaluations of [$^{18}$F]4F-MHPG.

During the development of the technology provided herein, experiments were performed to evaluate high specific activity [$^{18}$F]4F-MHPG made with embodiments of the radiosynthetic methods described herein. These results demonstrate that the methods provide the compounds at sufficiently high specific activities for clinical studies.

1.1. Isolated Rat Heart Study of High Specific Activity [$^{18}$F]4F-MHPG.

Figure 3:
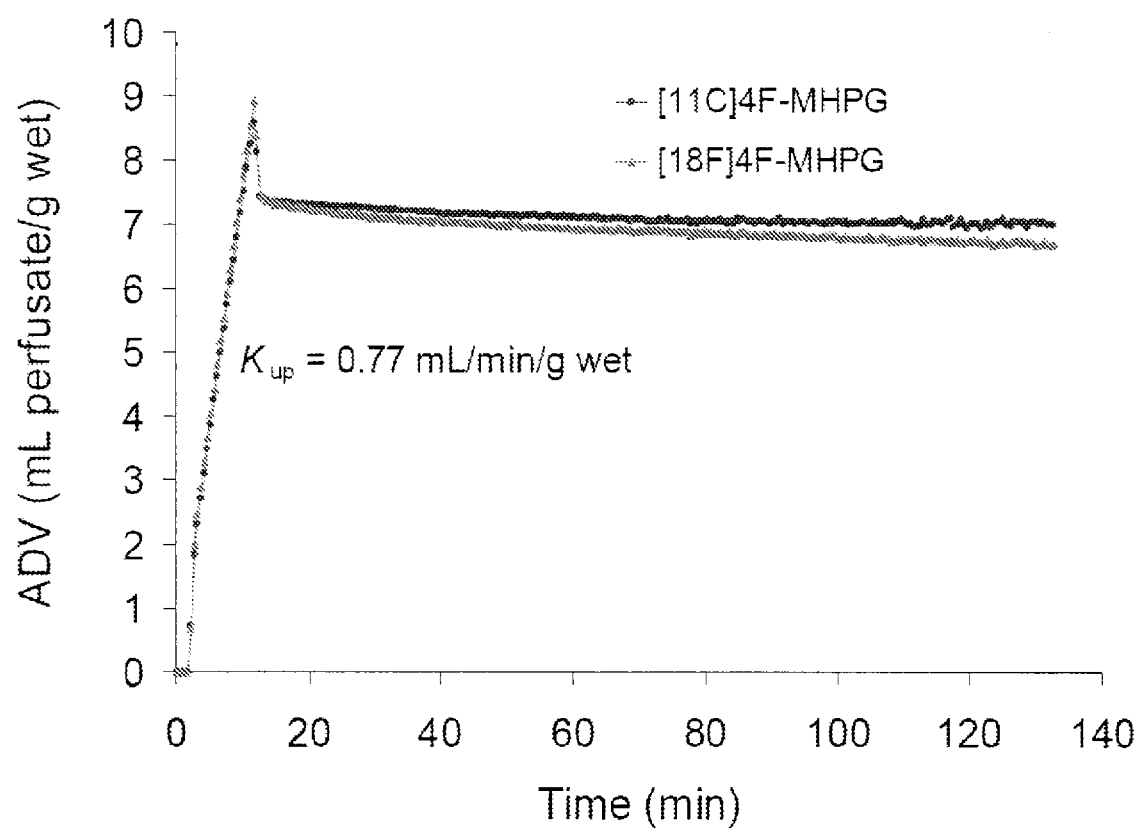
FIG. 3 is a plot showing the kinetics of [$^{11}$C]4F-MHPG and [$^{18}$F]4F-MHPG in isolated rat hearts.

Data were collected to determine the kinetics of [$^{18}$F]4F-MHPG in the isolated working rat heart model and these data were compared with a previous study of high specific activity [$^{11}$C]4F-MHPG (FIG. 3). The radiotracer was infused into the heart for 10 minutes to measure the tracer uptake rate into cardiac sympathetic neurons ($K_{up}$, shown in units of ml/min/g tissue wet). Then, the heart was infused with normal heart perfusate to measure the tracer clearance rate from the heart over 2 hours. As shown in FIG. 3, the kinetics of the two compounds are almost identical, independent of whether the 4F-MHPG compound is radiolabeled with carbon-11 or fluorine-18. As such, the kinetics of [$^{18}$F]4F-MHPG are almost identical to those of [$^{11}$C]4F-MHPG in the isolated rat heart. Moreover, these results demonstrate that [$^{18}$F]4F-MHPG has a long retention time inside sympathetic neurons ($T_{1/2}$>24 hours), which makes tracer kinetic modeling of myocardial kinetics in humans simpler and more robust than is currently possible with existing cardiac sympathetic nerve imaging agents.

1.2. Biological Studies of High Specific Activity [$^{18}$F]4F-MHPG in Non-Human Primates.

During the development of embodiments of the technology, several studies of [$^{18}$F]4F-MHPG were performed in rhesus macaque monkeys. These include assessments of image quality, in terms of relative uptake of the radiotracer into heart, lungs and liver; metabolic breakdown of [$^{18}$F] 4F-MHPG in blood; myocardial kinetics of [$^{18}$F]4F-MHPG and their quantitative analysis; specificity of [$^{18}$F]4F-MHPG for sympathetic nerve terminals through pharmacological blocking studies; and assessment of [$^{18}$F]4F-MHPG uptake into adrenal glands (to assess its potential application for oncology in imaging adrenergic tumors like pheochromocytoma and neuroblastoma).

1.2.1. MicroPET Imaging Studies of [$^{18}$F]4F-MHPG.

A series of microPET imaging studies were performed in the macaque model to assess image quality and tracer kinetics. In most of these the time course of the metabolic breakdown of [$^{18}$F]4F-MHPG in plasma was also determined. The studies are summarized below in Table 1.

TABLE 1

MicroPET studies of [$^{18}$F]4F-MHPG

| Date | Conditions | Organ Imaged | Imaging Time (min) | Metabolism study? |
|---|---|---|---|---|
| Feb. 3, 2011 | Control | Heart | 90 | No |
| Mar. 3, 2011 | Control | Heart | 90 | Yes |
| Mar. 17, 2011 | Control | Heart | 90 | Yes |
| Mar. 31, 2011 | Control | Heart | 90 | Yes |
| Apr. 7, 2011 | Control | Heart | 90 | Yes |
| May 5, 2011 | Control | Adrenal glands | 90 | No |
| Jun. 9, 2011 | Desipramine (DMI) block of NET | Heart & Adrenals | 90 | Yes |

Orthogonal slice images of cardiac sympathetic innervation from three of the control studies were acquired. The high quality images showed uniform left ventricular uptake of [$^{18}$F]4F-MHPG, consistent with uniform innervation in the left ventricle. There was also very low uptake of the compound in the lungs and liver. Liver uptake of [$^{18}$F]4F-MHPG is much lower than is typically seen with either [$^{11}$C]meta-hydroxyephedrine (HED) or [$^{123}$I]metaiodobenzylguanidine (MIBG), providing improved image contrast between heart tissue and nearby organs. Faint uptake in the spinal column bones suggests there is little in vivo defluorination of [$^{18}$F]4F-MHPG.

1.2.2 Metabolism of [$^{18}$F]4F-MHPG in Monkeys.

Figure 4A:
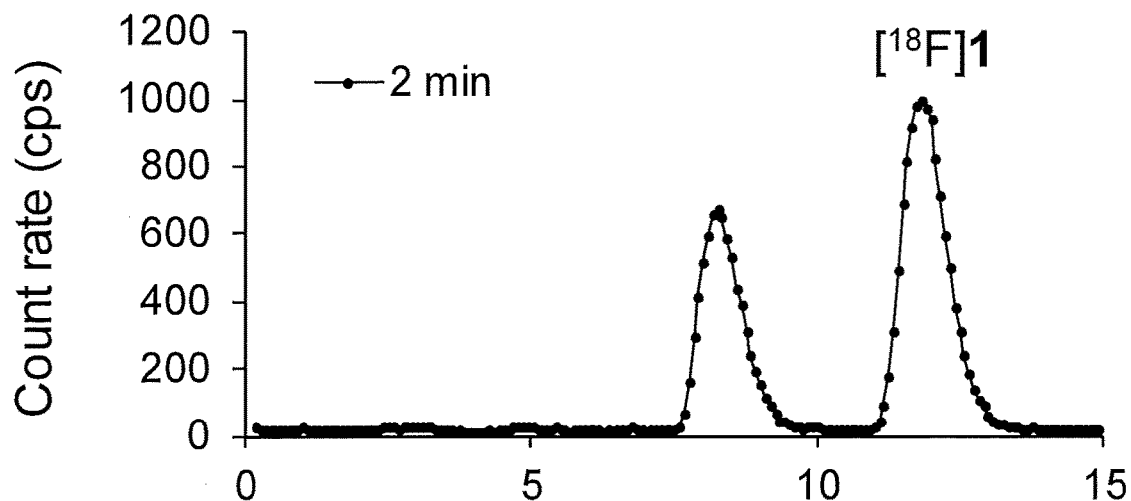
FIGS. 4A and 4B are plots showing reverse-phase HPLC analysis of [$^{18}$F]4F-MHPG and its metabolites in rhesus macaque plasma.
Figure 5:
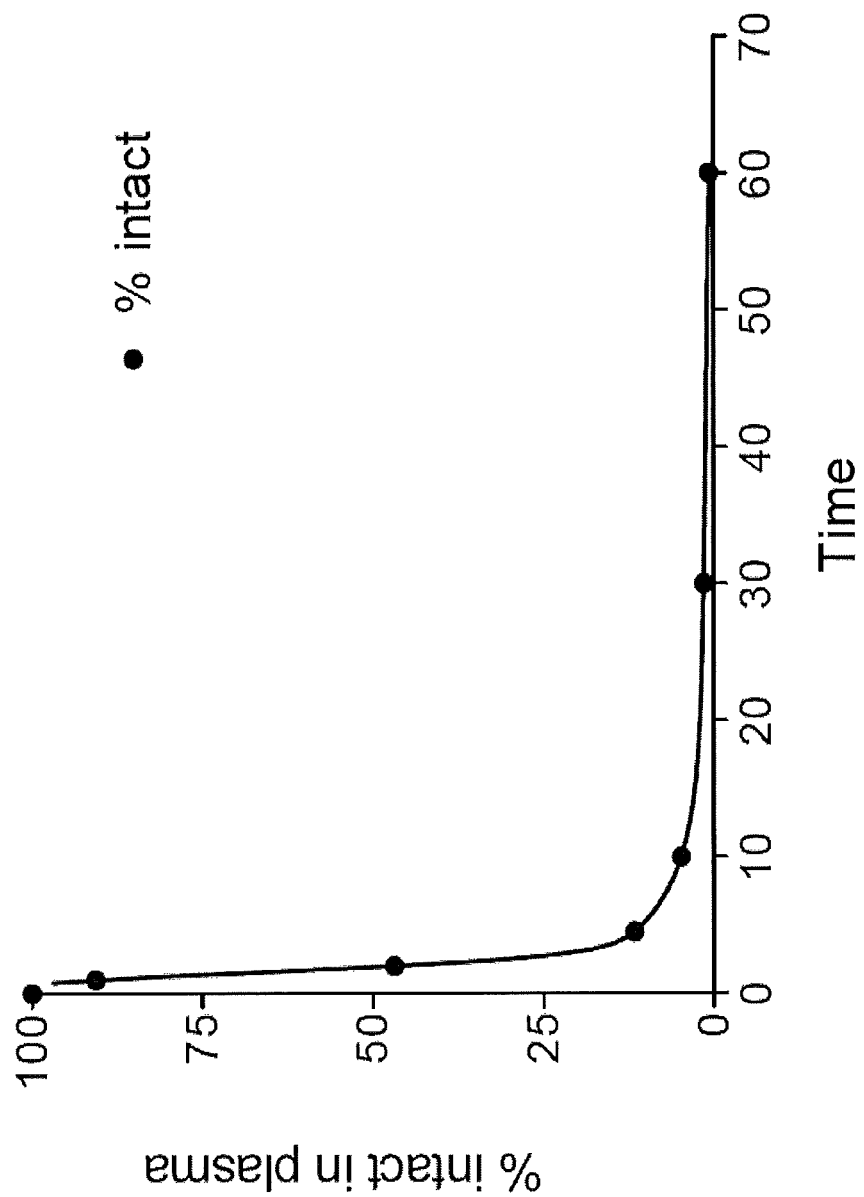
FIG. 5 is a plot showing metabolic breakdown of [$^{18}$F] 4F-MHPG in the plasma of a rhesus macaque monkey.

In some of the microPET studies, venous blood samples (e.g., n=6) were drawn to assess the metabolic breakdown of [$^{18}$F]4F-MHPG in plasma (see Table 1). Plasma was processed for injection onto a reverse-phase HPLC system equipped with a radiation detector. The percentages of intact parent tracer and radiolabeled metabolites were determined as a function of time. A representative HPLC trace for a blood sample drawn at t=2 minutes after injection is shown in FIG. 4A. In this system, [$^{18}$F]4-MHPG has a retention time $R_t$ of approximately 11.2 minutes while the main polar radiometabolite formed has an $R_t$ of approximately 7.9 minutes. These data show that [$^{18}$F]4-MHPG is metabolized relatively rapidly, e.g., in the rhesus monkey. Together, all of the data show that [$^{18}$F]4F-MHPG is rapidly metabolized in the plasma of rhesus monkeys (see, e.g., the example shown in FIG. 5).

Figure 4B:
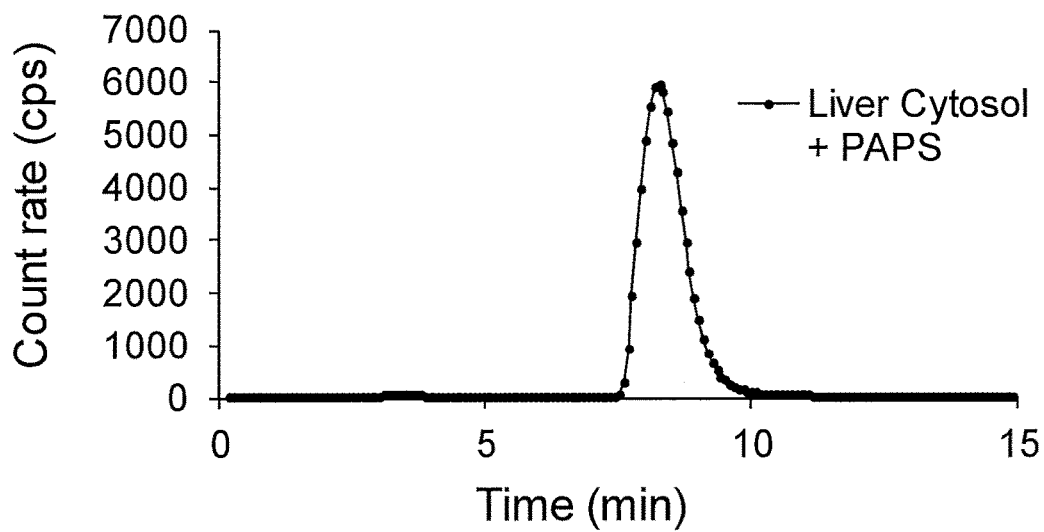
Figure 4C:
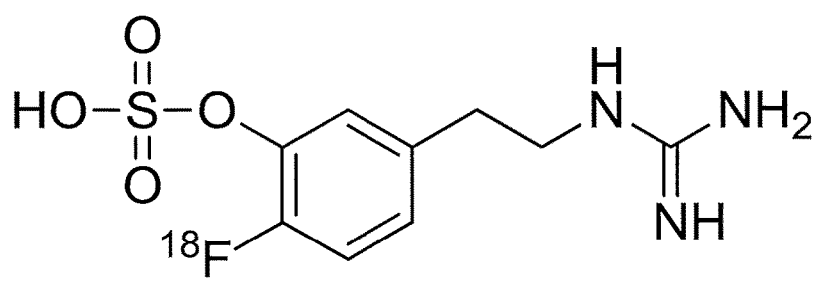
FIG. 4C shows the structure of the sulfur conjugated form.

The main radiometabolite formed is more polar than the parent compound, [$^{18}$F]4-MHPG. The metabolite has been identified as the sulfur conjugate of [$^{18}$F]4-MHPG based on in vitro incubations of the parent compound with a monkey liver cytosol fraction and the required cofactor 3'-phosphoadenosine-5'phosphosulfate (PAPS). After only 1 minute of in vitro incubation, approximately 70% of [$^{18}$F]4-MHPG was sulfur conjugated, and after 20 minutes of incubation, 100% was in the sulfur-conjugated form (FIG. 4B). Sulfur conjugation occurs at the meta-hydroxyl group (FIG. 4C). Without being bound by theory and without requiring an understanding of the mechanism to practice the technology, it is contemplated that rapid metabolism of [$^{18}$F]4F-MHPG is a reason for its low liver uptake. In comparison, the structurally similar carbon-11 compound, [$^{11}$C]guanylmeta-octopamine (GMO), has a slower metabolic breakdown in monkey plasma, with a $T_{1/2}$ for breakdown of approximately 13 minutes.

Many tracers are metabolized more quickly in monkeys than in humans, e.g., tracer metabolism rates are typically 2 to 3 times slower in humans than in monkeys. In some embodiments, a longer lifetime in human subjects is advantageous, e.g., to allow cardiac neurons to accumulate the tracer for a longer period of time, thus providing more kinetic data for quantitative analyses. In addition, a metabolism rate that is 2 to 3 times slower in humans allows an imaging study of approximately 30 minutes to provide all the kinetic data needed for quantifying cardiac nerve density. Also, metabolic breakdown essentially "inactivates" the tracer, which could increase its safety in humans. Since [$^{18}$F]4-MHPG may have some activity as a depletor of norepinephrine from storage vesicles in sympathetic neurons, it may prove beneficial to have it completely metabolized to the sulfur conjugate within 1 hour after injection into a human subject.

1.2.3 Myocardial Kinetics of [$^{18}$F]4F-MHPG

Figure 6:
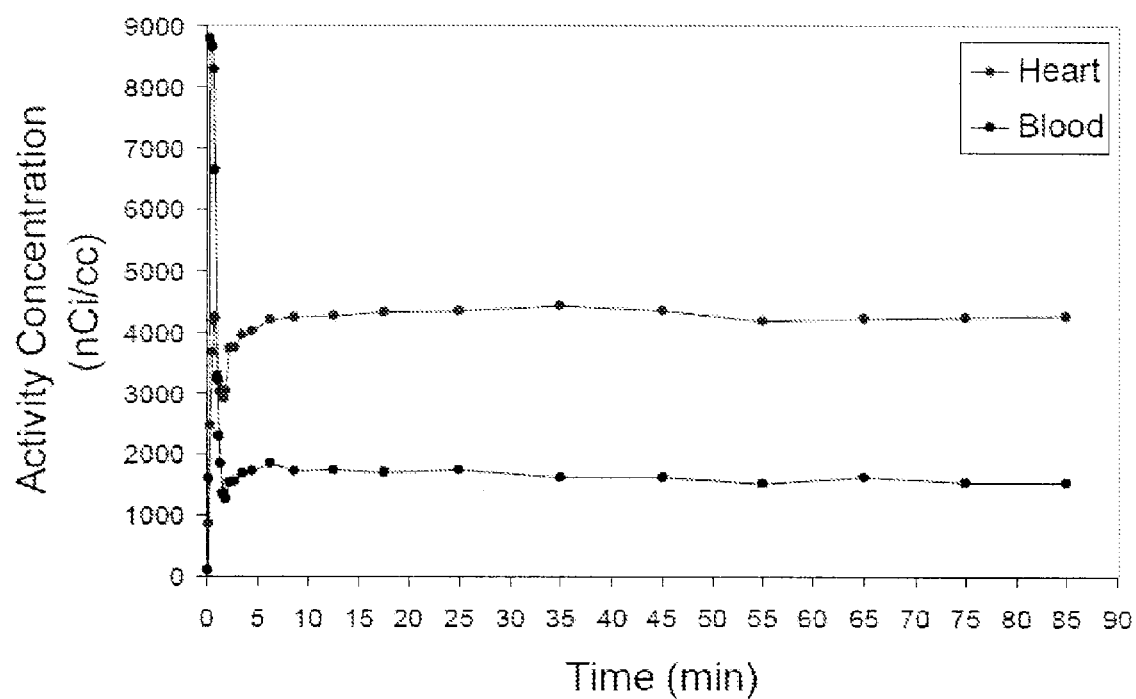
FIG. 6 is a plot showing kinetics of [$^{18}$F]4F-MHPG in whole blood (lower trace) and left ventricle (top trace) in a rhesus macaque monkey.

The kinetics of [$^{18}$F]4-MHPG in monkeys are shown in FIG. 6. In blood, after the peak of the bolus injection, blood activity levels stay roughly constant from approximately 5-10 minutes to the end of the study (e.g., approximately 85 minutes). Because of the relatively rapid metabolism (e.g., by sulfur conjugation) of [$^{18}$F]4-MHPG, after 10-20 minutes most of the activity in blood is in the form of the sulfur conjugate of [$^{18}$F]4-MHPG. Myocardial activity climbs for about 15-30 minutes after injection and then remains constant. The lack of any further accumulation of [$^{18}$F]4-MHPG into cardiac nerve terminals after this time is indirect evidence that the sulfur conjugate of [$^{18}$F]4-MHPG is inactive at the norepinephrine transporter (NET). Thus only intact 'parent' tracer molecules of [$^{18}$F]4-MHPG are capable of being taken up into presynaptic sympathetic nerve terminals. Based on a predicted slower metabolism of [$^{18}$F]4-MHPG in humans than in monkeys, the tracer is expected to accumulate for a longer time than is seen in monkeys.

During the development of embodiments of the technology provided herein, the kinetics of [$^{18}$F]4F-MHPG in monkey hearts was assessed using either compartmental modeling or Patlak graphical analysis to obtain quantitative measures of regional cardiac sympathetic nerve density.

Figure 7:
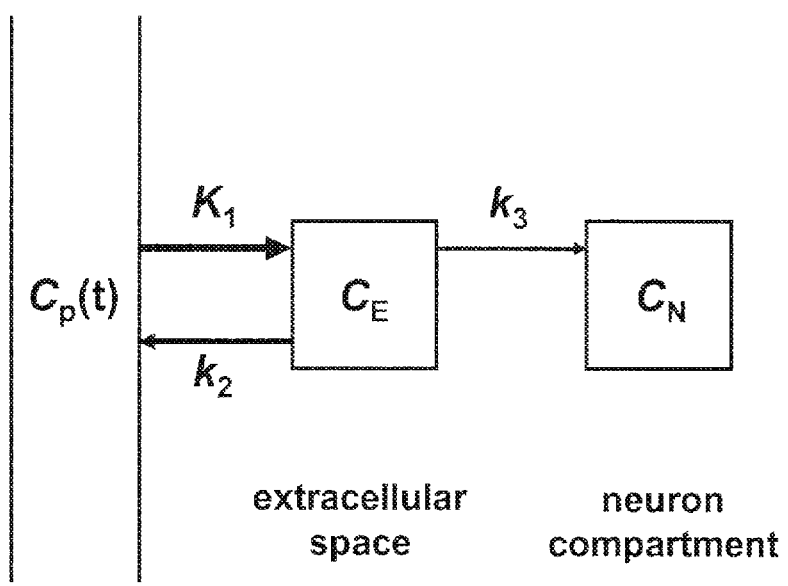
FIG. 7 is a diagram showing a compartmental model used to analyze the myocardial kinetics of [$^{18}$F]4F-MHPG.
Figure 8:
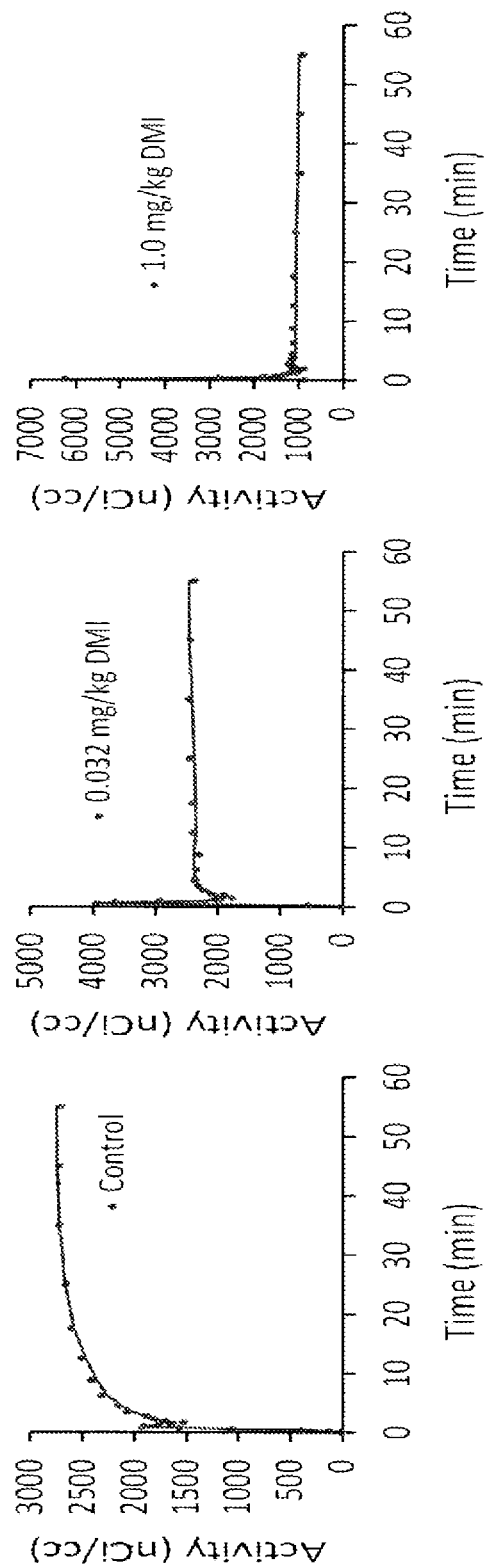
FIG. 8 is a series of plots showing compartmental modeling of [$^{18}$F]4F-MHPG kinetics in monkeys for control (left), moderate desipramine (DMI) dose blockade of cardiac NET (middle), and high DMI dose (right).
Figure 9:
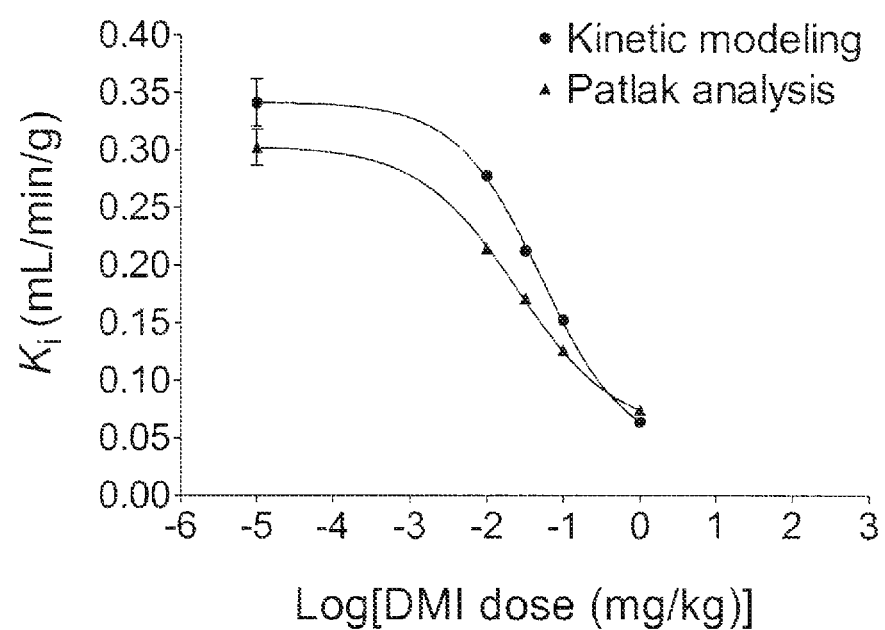
FIG. 9 is a plot showing dose-response curves of net uptake constants $K_i$(ml/min/g) derived from either kinetic compartmental modeling (circles) or Patlak graphical analysis (triangles) of [$^{18}$F]4F-MHPG kinetics in rhesus macaque monkeys.

For some analyses, a simplified compartmental model that assumed irreversible trapping inside nerve terminals was used to estimate the model rate constants $K_1$ (ml/min/g), $k_2$ (min$^{-1}$), $k_3$ (min$^{-1}$), and a blood volume fraction BV (dimensionless) (see, e.g., FIG. 7). In both the control studies and DMI blocking studies, the model quickly converged to a single global minimum in just a few iterations of the nonlinear regression analysis (FIG. 8). The rate constant $k_3$, which reflects the neuronal uptake rate of the tracer, did not decline in proportion to increasing doses of DMI. This shows that a fit of the model to the data is provided by adjusting rate constants other than $k_3$. Combining the rate constants $K_1$, $k_2$, and $k_3$ into a 'net uptake rate constant' $K_i$ (ml/min/g)=($K_1k_3$)/($k_2+k_3$) provides for control studies that $K_i$=0.341±0.041 ml/min/g. This aggregate parameter provides a stable measure of cardiac nerve density that declined in a dose-dependent manner with increasing DMI dose (FIG. 9, "Kinetic modeling"). These results show that compartmental modeling of [$^{18}$F]4F-MHPG kinetics in human heart provides accurate and sensitive quantitative measures of regional cardiac sympathetic nerve density.

For some analyses, Patlak graphical analysis was used, which uses a mathematical transformation of the kinetic data $C_p(t)$ and $C_t(t)$ to generate a 'Tatlak plot' having a characteristic linear phase (see, e.g., Patlak and Blasberg (1985) "Graphical evaluation of blood-to-brain transfer constants from multiple-time uptake data. Generalizations." *J Cereb Blood Flow* 5: 584-90). The slope of the linear portion of a Patlak plot, $K_p$ (ml/min/g), provides an alternate estimate of the 'net uptake rate constant' $K_i$ (ml/min/g). Thus, for the model structure used (FIG. 7), the slope of the Patlak plot is given by $K_p \approx (K_1k_3)/(k_2+k_3)$.

Figure 10:
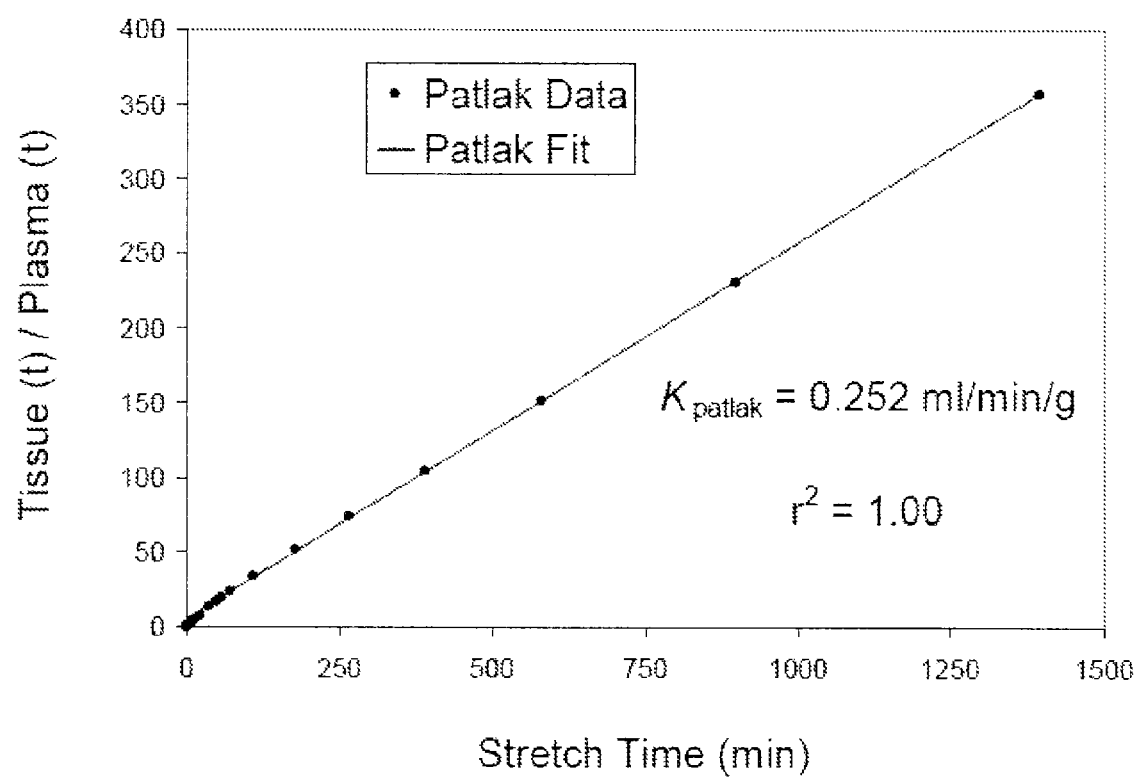
FIG. 10 is a plot showing Patlak analysis of the myocardial kinetics of [$^{18}$F]4F-MHPG kinetics in rhesus macaque monkey.

During the development of embodiments of the technology provided herein, the myocardial kinetics of [$^{18}$F]4F-MHPG was assessed using Patlak graphical analysis and metabolite-corrected plasma input functions. Patlak graphical analysis of one of the control studies in a rhesus macaque monkey is shown in FIG. 10. In this example, the Patlak plot is highly linear ($r^2$=1.00) and the estimated Patlak slope $K_{patlak}$=0.252 ml/min/g. These data show that a tracer possessing a relatively slow NET transport rate and very efficient intraneuronal trapping inside storage vesicles is appropriate for analysis using the Patlak graphical method. As such, regional estimates of the Patlak slope from Patlak analysis of the kinetics of [$^{18}$F]4F-MHPG serve as robust measures of regional cardiac sympathetic nerve density in patients with heart diseases.

Figure 11:
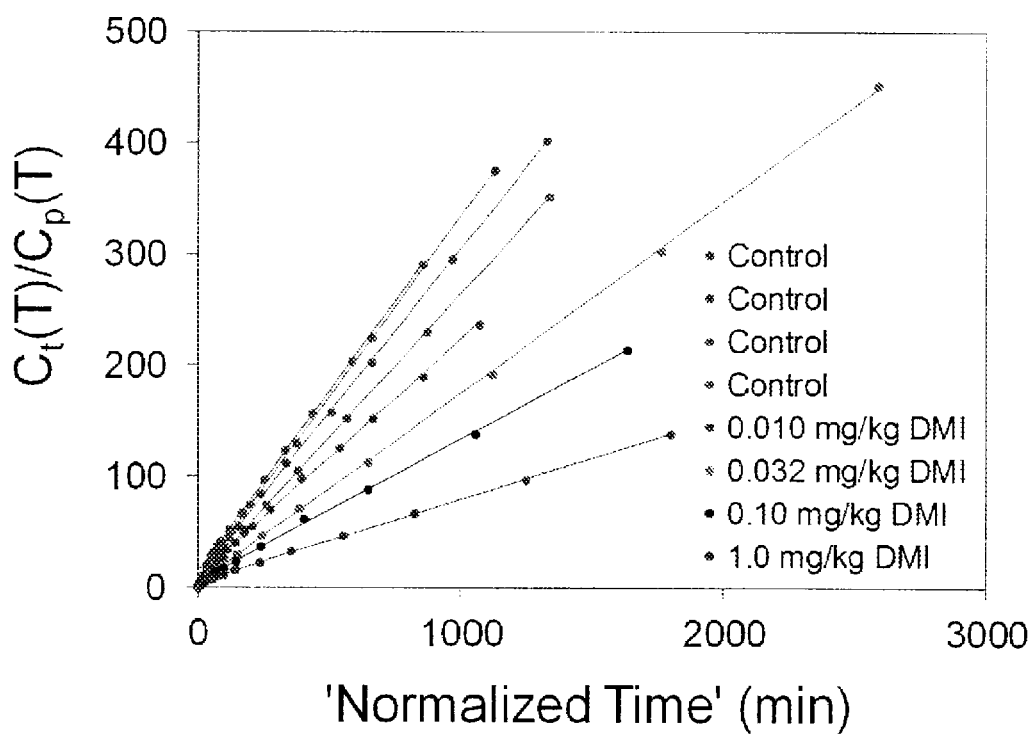
FIG. 11 is a plot showing Patlak analysis of the myocardial kinetics of [$^{18}$F]4F-MHPG in rhesus macaque monkey.

Additional data were collected and Patlak analyses performed. In these experiments, for the control studies, the Patlak plots were highly linear ($r^2$>0.99) with an average measured Patlak slope $K_p$=0.302±0.031 ml/min/g (FIG. 11). For the four different DMI block studies, the data were best fit with linear Patlak plots and the measured Patlak slopes declined in a DMI-dose dependent manner (FIG. 9, "Patlak analysis"). The decline in the estimated $K_i$ or $K_p$ values with increasing doses of DMI each followed a sigmoidal dose-response curve (FIG. 9). For the $K_i$ data from compartmental modeling, a half-maximal inhibitory concentration ($IC_{50}$) of 0.051 mg/kg DMI was estimated, with a Hill slope $n_H$=−0.79. For the $K_p$ data, $IC_{50}$=0.025 mg/kg DMI and $n_H$=−0.68.

These results suggest that estimates of the 'net uptake rate' constant $K_i$, obtained from either compartmental modeling or Patlak analysis of [$^{18}$F]4F-MHPG kinetics, are sensitive and robust measures of regional cardiac sympathetic nerve density. In addition, these data demonstrate that the quantitative analysis methods work over a wide range of nerve densities, as produced experimentally with pharmacological blockade of norepinephrine transporters (NET) using the drug desipramine (DMI).

1.2.4 Desipramine (DMI) Block of the Neuronal Uptake of [$^{18}$F]4F-Mhpg

To verify that presynaptic sympathetic nerve terminals are the main locus of retention of [$^{18}$F]4F-MHPG ([$^{18}$F]4F-MHPG) in the heart, data were collected from microPET imaging in a monkey that had been administered a blocking dose of the potent NET inhibitor desipramine (DMI). Orthogonal slice images were acquired for comparison with data from a control study. By comparing microPET images of [$^{18}$F]4F-MHPG in a control monkey following different levels of DMI block of NET, the data show that increased levels of DMI block of NET transporters on presynaptic sympathetic nerve terminals led to a progressive decline in the cardiac retention of the [$^{18}$F]4F-MHPG tracer in myocardial tissue and/or prevents any significant cardiac retention of the [$^{18}$F]4F-MHPG tracer. At the highest DMI block conditions (1.0 mg/kg), myocardial levels of [$^{18}$F]4F-MHPG are lower than the levels in blood, indicating complete blockade of the retention of the tracer in the heart. The data showed that [$^{18}$F]4F-MHPG is 100% specific for cardiac sympathetic neurons, with very low nonspecific binding.

As such, myocardial uptake of [$^{18}$F]4F-MHPG under control conditions is 100% specific to sympathetic nerve terminals. Also, in the DMI block images, data from the highest dose DMI block study demonstrated that nonspecific binding in heart tissue outside sympathetic nerve terminals is extremely low. Thus, in some embodiments, quantitative measures based on kinetics and/or retention of [$^{18}$F]4F-MHPG provide accurate measures of nerve density over a wide dynamic range, from normal levels down to the very low levels seen in diseases that cause severe denervation, such as diabetic autonomic neuropathy and Parkinson's disease. As such, for this and other reasons the compounds are contemplated to find use in diseases that cause severe denervation, such as diabetic autonomic neuropathy and Parkinson's disease 1.2.5 Oncology Applications: Uptake of [$^{18}$F]4F-MHPG into Adrenal Glands To assess the ability of [$^{18}$F]4F-MHPG to serve an additional clinical role as a marker of adrenergic tumors such as neuroblastoma and pheochromocytoma, data were collected to examine the uptake of [$^{18}$F]4F-MHPG into the adrenal gland. In control studies, the adrenal glands took up sufficient [$^{18}$F]4F-MHPG to be visualized, especially on the right side of the transaxial images, which was better separated from the kidney than the contralateral adrenal gland. There was also significant uptake in the cortex of the kidney. The kinetics of [$^{18}$F]4F-MHPG in the adrenal gland are very similar to those seen in the heart. In the DMI block study above, the adrenal glands were scanned for 10 minutes following the 90 minute cardiac study. No uptake of [$^{18}$F]4F-MHPG was seen in the adrenal glands, demonstrating that [$^{18}$F]4F-MHPG uptake into the adrenal gland is primarily mediated by NET transport.

In images comparing the uptake of [$^{18}$F]4F-MHPG into the adrenal glands of a control monkey and following DMI block of NET uptake, controls show a high uptake into the renal cortex as well as into the adrenal gland while the images from experiments testing DMI block conditions showed that [$^{18}$F]4F-MHPG uptake into the adrenals is completely absent. These results indicate that adrenal uptake of [$^{18}$F]4F-MHPG is specific to NET transport.

These data demonstrate that [$^{18}$F]4F-MHPG images adrenal glands and is thus a tracer for adrenergic tumors (e.g., pheochromocytoma, neuroblastoma, etc.) using PET scanning technologies. Together, these data show that this agent finds use in oncology applications in the nuclear medicine clinic, e.g., for use similar to the use of $^{123}$I-meta-iodobenzyl-guanidine (under the trade name 'AdreView', GE Healthcare) for oncology applications, and now, more recently as a potential cardiac sympathetic nerve imaging agent (see, e.g., Jacobson et al. (2010) "Myocardial iodine-123 meta-iodobenzylguanidine imaging and cardiac events in heart failure: results of the prospective ADMIRE-HF (AdreView Myocardial Imaging for Risk Evaluation in Heart Failure) study", J Am Coll Cardiol. 55: 2212-21).

1.2.6 Biodistribution in a Mammal

During the development of embodiments of the technology, data were collected from bioevaluation studies of [$^{18}$F]4F-MHPG. In particular, biodistribution studies in rats showed that the tissue distribution of low specific activity [$^{18}$F]4F-MHPG was similar to the distribution of the carbon-11 labeled analog [$^{11}$C]4F-MHPG (Table 2). Table 2 shows the tissue concentrations of the compounds (expressed as a percentage of the injected dose per gram) at 30 minutes after injection in rats. A number of 5 rats was tested in each study (n=5).

TABLE 2

| Tracer | left ventricle | lung | liver | muscle | spleen | adrenal medulla | blood |
|---|---|---|---|---|---|---|---|
| Biodistribution in rat | | | | | | | |
| [$^{11}$C]4F-MHPG | 1.77 ± 0.27 | 0.56 ± 0.15 | 1.22 ± 0.18 | 0.07 ± 0.01 | 0.52 ± 0.10 | 0.56 ± 0.21 | 0.08 ± 0.01 |
| [$^{18}$F]4F-MHPG | 1.45 ± 0.13 | 0.43 ± 0.08 | 1.14 ± 0.16 | 0.07 ± 0.01 | 0.56 ± 0.10 | 0.54 ± 0.08 | 0.07 ± 0.01 |

1.2.7 Radiation Absorbed Dose Estimates

During the development of embodiments of the technology provided herein, the biodistribution of [$^{18}$F]4F-MHPG into the organs of rats was assessed. In particular, four time points (Table 3) were collected and used to derive human radiation absorbed dose estimates using the OLINDA/EXM 1.0 software package (see, e.g., Stabin et al. (2005) "OLINDA/EXM; the second-generation personal computer software for internal dose assessment in nuclear medicine", J Nucl Med. 46: 1023-7). From the acquired data, the maximum percentage of the injected dose observed in the gastrointestinal tract (12.6%) was assumed to enter the small intestine using the ICRP 30 GI Tract model incorporated into the OLINDA/EXM program. Also, in separate microPET imaging studies in rats, 19.9±0.2% of the injected dose was found to be excreted through the bladder with a biological half-time of 0.20±0.02 hours. These values were entered into the Dynamic Bladder model of OLINDA/EXM, assuming a 4.0-hour void interval. Absorbed dose estimates for the reference adult male organ model of OLINDA/EXM are shown in Table 4. Organs with the highest absorbed dose estimates included the urinary bladder wall (0.666 rad/mCi), upper lower intestine (0.221 rad/mCi), small intestine (0.201 rad/mCi), and the heart wall (0.201 rad/mCi). An 'effective dose' of 0.091 rem/mCi was estimated for [$^{18}$F]4F-MHPG. Under United States Federal Regulations governing research with a new radiopharmaceutical (21 CFR § 361.1), the maximum allowable radiation absorbed dose to an individual organ (other than the gonads) is 5 rad. Considering the maximum estimated absorbed dose (urinary bladder wall; 0.666 rad/mCi), initial PET studies in human subjects could use a maximum of 7.5 mCi of [$^{18}$F]4F-MHPG. This would correspond to an 'effective dose' of 0.68 rem.

TABLE 3

Biodistribution of [$^{18}$F]4F-MHPG into major organs in rats (% ID · kg/g)

| Organ | 5 min | 30 min | 60 min | 120 min |
|---|---|---|---|---|
| Brain | 0.004 ± 0.001 | 0.003 ± 0.000 | 0.002 ± 0.000 | 0.001 ± 0.001 |
| Eyeballs | 0.039 ± 0.006 | 0.040 ± 0.004 | 0.041 ± 0.006 | 0.026 ± 0.006 |
| Heart | 0.746 ± 0.067 | 0.602 ± 0.111 | 0.526 ± 0.116 | 0.347 ± 0.055 |
| Lung | 0.267 ± 0.045 | 0.136 ± 0.032 | 0.091 ± 0.015 | 0.036 ± 0.006 |
| Liver | 0.477 ± 0.110 | 0.406 ± 0.071 | 0.350 ± 0.077 | 0.233 ± 0.049 |
| Pancreas | 0.137 ± 0.024 | 0.145 ± 0.021 | 0.172 ± 0.042 | 0.121 ± 0.016 |
| Spleen | 0.268 ± 0.044 | 0.262 ± 0.055 | 0.253 ± 0.054 | 0.235 ± 0.066 |
| Adrenal | 0.203 ± 0.083 | 0.181 ± 0.069 | 0.193 ± 0.053 | 0.133 ± 0.021 |
| Kidney | 1.398 ± 0.530 | 0.183 ± 0.055 | 0.186 ± 0.090 | 0.078 ± 0.024 |
| Stomach | 0.116 ± 0.021 | 0.110 ± 0.004 | 0.115 ± 0.029 | 0.089 ± 0.019 |
| Ovary* | 0.194 ± 0.048 | 0.171 ± 0.020 | 0.142 ± 0.052 | 0.129 ± 0.029 |
| Uterus* | 0.268 ± 0.044 | 0.155 ± 0.001 | 0.112 ± 0.046 | 0.081 ± 0.006 |
| Testes* | 0.018 ± 0.002 | 0.010 ± 0.001 | 0.008 ± 0.003 | 0.004 ± 0.001 |
| Muscle† | 0.019 ± 0.005 | 0.025 ± 0.011 | 0.016 ± 0.002 | 0.015 ± 0.002 |
| Bone† | 0.060 ± 0.015 | 0.039 ± 0.015 | 0.027 ± 0.009 | 0.016 ± 0.005 |
| Blood† | 0.062 ± 0.004 | 0.022 ± 0.003 | 0.016 ± 0.002 | 0.009 ± 0.001 |

*(n = 2) animals used for these values.
†Values expressed as % ID/g.

TABLE 4

Radiation absorbed dose estimates (rem/mCi) for [$^{18}$F]4F-MHPG for the reference adult male model of OLINDA/EXM 1.0

| Target organ | Total dose | Dose for 10 mCi |
|---|---|---|
| | (rad/mCi) | (rad) |
| Adrenals | 0.059 | 0.59 |
| Brain | 0.025 | 0.25 |
| Breasts | 0.026 | 0.26 |
| Gallbladder wall | 0.061 | 0.61 |
| LLI wall | 0.107 | 1.07 |
| Small intestine | 0.201 | 2.01 |
| Stomach wall | 0.048 | 0.48 |
| ULI wall | 0.221 | 2.21 |
| Heart wall | 0.109 | 1.09 |
| Kidneys | 0.078 | 0.78 |
| Liver | 0.096 | 0.96 |
| Lungs | 0.035 | 0.35 |
| Muscle | 0.037 | 0.37 |

TABLE 4-continued

Radiation absorbed dose estimates (rem/mCi) for [$^{18}$F]4F-MHPG for the reference adult male model of OLINDA/EXM 1.0

| Target organ | Total dose | Dose for 10 mCi |
|---|---|---|
| Ovaries | 0.088 | 0.88 |
| Pancreas | 0.063 | 0.63 |
| Red marrow | 0.037 | 0.37 |
| Osteogenic cells | 0.049 | 0.49 |
| Skin | 0.026 | 0.26 |
| Spleen | 0.079 | 0.79 |
| Testes | 0.041 | 0.41 |
| Thymus | 0.033 | 0.33 |
| Thyroid | 0.029 | 0.29 |
| Urinary bladder wall | 0.666 | 6.66 |
| Uterus | 0.103 | 1.03 |
| Total body | 0.041 | 0.41 |
| | (rem/mCi) | (rem) |
| Effective dose | 0.091 | 0.91 |

Example 2

Studies of $^{18}$F-labeled Aryl-Y-alkylguanidine Compounds

During the development of the technology provided herein, data were collected to characterize $^{18}$F-labeled aryl-Y-alkylguanidine compounds (in which Y is O, S, or NH) for use as PET tracers. Experiments were conducted to evaluate closely related analogs such as $^{11}$C-labeled analogs of phenoxyethylguanidine as imaging agents for cardiac sympathetic innervation and adrenergic tumors in an isolated rat heart system (Table 5).

TABLE 5

11C-labeled phenoxyethylguanidines

| Name | Structure (carbon-11 = *) |
|---|---|
| 11C-phenoxyethylguanidine (11C-PEG) | (phenyl-O-CH2-CH2-NH-C*(=NH)-NH2) |
| 11C-meta-hydroxy-phenoxyethylguanidine (11C-MHPEG) | (3-HO-phenyl-O-CH2-CH2-NH-C*(=NH)-NH2) |
| 11C-4-fluoro-phenoxyethylguanidine (11C-4F-PEG) | (4-F-phenyl-O-CH2-CH2-NH-C*(=NH)-NH2) |

C-11 compounds are generally easier to synthesize than F-18 compounds. However, F-18 compounds demonstrate better imaging characteristics. As such, for some studies, C-11 compounds are first synthesized and tested, and then promising candidates are synthesized using F-18 rather than C-11. Experiments testing C-11 compounds at least demonstrate that a particular class of compounds has members that function well as imaging agents. Then, effective C-11 compounds having a ring fluorine indicate that placing an F-18 into that particular location will also produce an effective compound with improved imaging characteristics. As such, the use of C-11 labeled analogs is an efficient tool for screening compounds that could potentially be F-18 labeled.

Experiments were conducted to test 11C-phenoxyethylguanidine (PEG), e.g., to establish baseline values for the NET transport rate ($K_{up}$, expressed in units of mL perfusate/min/g wet) and the clearance rate from sympathetic neurons ($T_{1/2}$, expressed in units of hours). See FIG. 12. This compound had a neuronal uptake rate of 5.37 mL/min/g wet, which is amongst the fastest observed in any experiment, and cleared with a major half-time of 5.7 hours.

Figure 12:
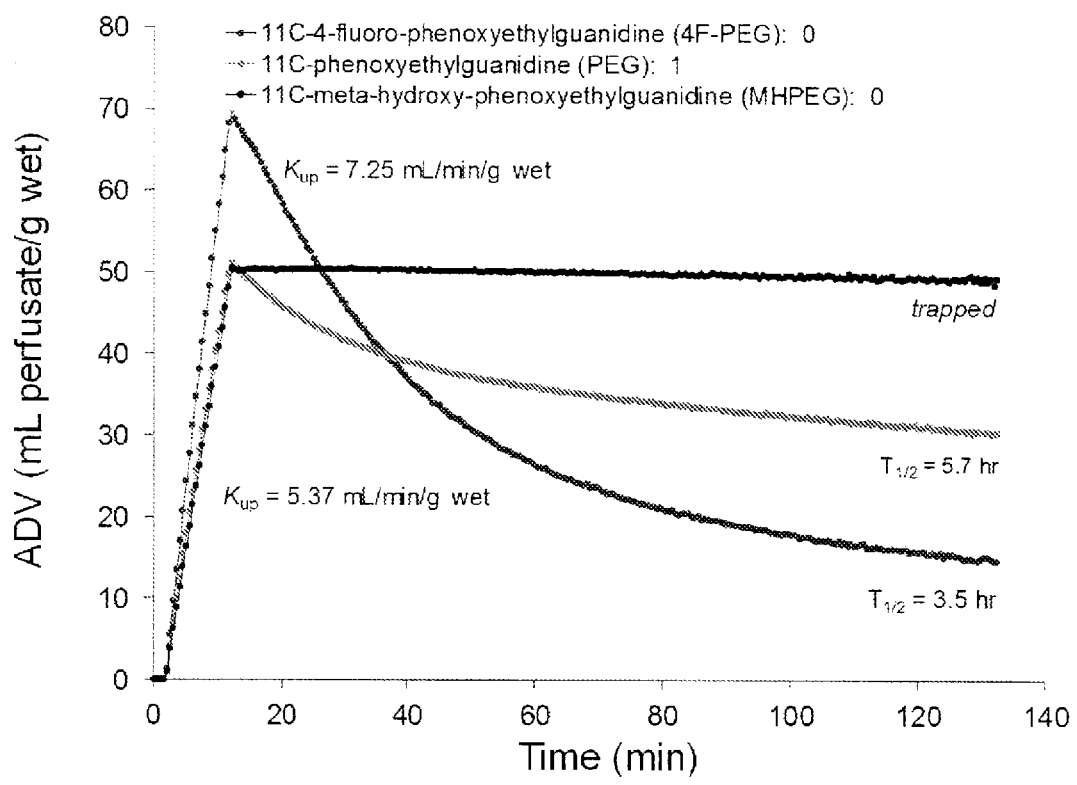
FIG. 12 is a plot showing rapid neuronal uptake of $^{11}$C-labeled phenoxyethylguanidines in an isolated rat heart model.

Next, experiments tested a ring-fluorine analog, 11C-4-fluoro-phenoxyethylguanidine (4F-PEG), to assess the influence of a fluorine on the neuronal uptake and clearance kinetics in the isolated rat heart. 4F-PEG had a faster transport rate that the PEG analog, viz., 7.25 mL/min/g wet, and cleared with a major half-time of 3.5 hours (FIG. 12). The 4-[18F]fluoro-phenoxyethylguanidine (4-[18F]F-PEG) is anticipated and contemplated to have nearly identical uptake and clearance, thus providing attractive characteristics for an imaging agent. It is further contemplated that the methods provided herein are applicable to synthesize 4-[18F]fluoro-phenoxyethylguanidine.

A 11C-meta-hydroxy-phenoxyethylguanidine (MHPEG) was also tested to evaluate if a small structural change in the compound led to efficient vesicular trapping, as had been observed previously in studies with a series of phenethylguanidine compounds. As predicted, this structural change led to complete trapping of MHPEG (FIG. 12), while still retaining a rapid neuronal uptake rate of 5.37 mL/min/g wet.

Figure 13:
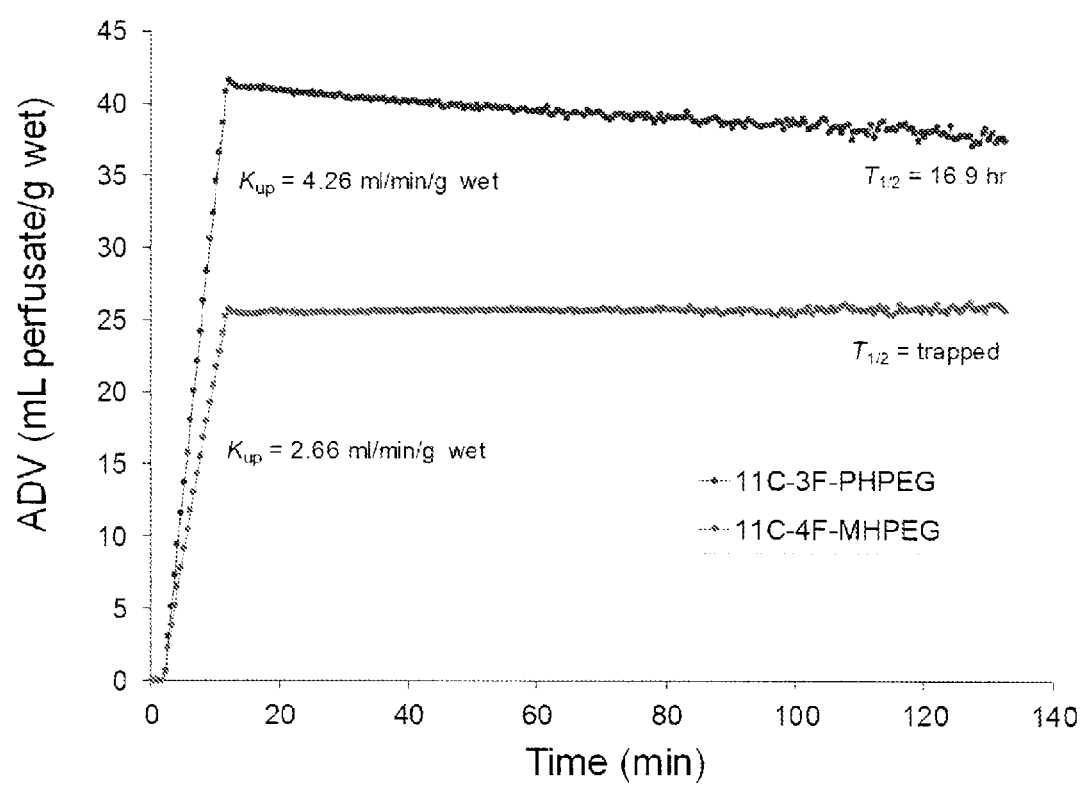
FIG. 13 is a plot showing the rapid neuronal uptake and long neuronal retention times of $^{11}$C-labeled fluoro-phenoxyethylguanidines in the isolated rat heart model.

Based on the results with 11C-4-fluoro-meta-hydroxy-phenethylguanidine (11C-4F-MHPG) and 4-[18F]fluoro-meta-hydroxy-phenethylguanidine ([18F]4F-MHPG), it was predicted that the corresponding analogs, 11C-4-fluoro-meta-phenoxyethylguanidine (11C-4F-MHPEG) and 4-[18F]fluoro-meta-hydroxy-phenoxyethylguanidine (4-[18F]-MHPEG) would likely be tracers with rapid NET transport and efficient storage in vesicles. To test this prediction, 11C-4F-MHPEG and its positional isomer, 11C-3-fluoro-para-hydroxy-phenoxyethylguanidine (11C-3F-PHPEG), were synthesized. Isolated rat heart studies with these two agents demonstrated rapid uptake rates with very long retention times (FIG. 13). 11C-4F-MHPEG had a neuronal uptake rate of 2.66 mL/min/g wet and was effectively trapped inside storage vesicles. 11C-3F-PHPEG had a faster uptake rate of 4.26 mL/min/g wet and cleared with a major half time of 16.9 hour.

Because of their rapid uptake rates and long retention times, these compounds (e.g., labeled with either carbon-11 or fluorine-18) are contemplated to find use as PET imaging agents, e.g., for localizing adrenergic tumors. Additional biological studies may reveal other uses of these imaging agents. According to the technology provided herein, it is straightforward to use the new 18F-labeling methods described herein to prepare 4-[18F]-MHPEG, as well as other compounds in this class.

Example 3

Studies of Guanoxan Compounds

During the development of embodiments of the technology provided herein, 11C-guanoxan (11C-GOX) was synthesized and experiments were conducted to evaluate its kinetics in the isolated rat heart (Table 6). In addition, data were acquired in studies of the kinetics of two ring-hydroxylated analogs of guanoxan: 11C-7-hydroxy-guanoxan (11C-7H-GOX) and 11C-6-hydroxy-guanoxan (11C-6H-GOX) (FIG. 14). Of the two ring hydroxylated analogs, the 7-hydroxy analog demonstrated a more rapid uptake and a longer retention time.

TABLE 6

$^{11}$C-labeled guanoxans

| Name | Structure (carbon-11 = *) |
|------|---------------------------|
| $^{11}$C-guanoxan ($^{11}$C-GOX) | |
| $^{11}$C-7-hydroxy-guanoxan ($^{11}$C-7H-GOX) | |
| $^{11}$C-6-hydroxy-guanoxan ($^{11}$C-7H-GOX) | |

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

We claim:

1. A compound comprising a structure according to:

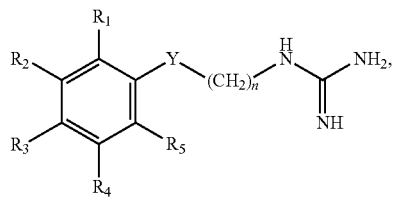

wherein
Y is O;
n is 1, 2, or 3;
one of $R_1$-$R_5$ is $^{18}$F; and
each of $R_1$-$R_5$, when not $^{18}$F, is independently selected from the group consisting of halo, hydroxy, and hydrogen.

2. The compound according to claim 1 wherein n is 2.
3. The compound according to claim 1 wherein
at least one of $R_2$-$R_4$ is hydroxy; and
each of $R_1$-$R_5$, when not $^{18}$F or hydroxy, is hydrogen.
4. The compound according to claim 1 wherein
n is 2,
at least one of $R_2$-$R_4$ is hydroxy; and
each of $R_1$-$R_5$, when not $^{18}$F or hydroxy, is hydrogen.
5. A radiotracing composition comprising a compound according to claim 1.
6. The radiotracing composition according to claim 5 further comprising a physiologically acceptable carrier.
7. The radiotracing composition of claim 5 formulated for intravenous administration.
8. The radiotracing composition of claim 5 formulated for systemic administration.
9. An iodonium salt precursor of the compound according to claim 1, wherein said iodonium salt precursor has a structure according to:

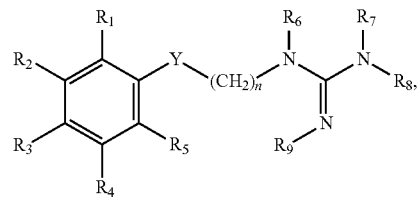

wherein
Y is O;
n is 1, 2, or 3;
one of $R_1$-$R_5$ comprises iodonium;
each of $R_1$-$R_5$, when not comprising iodonium, is independently selected from the group consisting of halo, protected hydroxy, and hydrogen; and
each of $R_6$-$R_9$ comprises a nitrogen-protecting group.
10. The iodonium salt precursor according to claim 9 wherein n is 2.
11. The iodonium salt precursor according to claim 9 wherein at least one of $R_2$-$R_4$ is protected hydroxy; and
each of $R_1$-$R_5$, when not comprising iodonium or protected hydroxy, is hydrogen.
12. The iodonium salt precursor according to claim 9 wherein
n is 2,
at least one of $R_2$-$R_4$ is protected hydroxy; and
each of $R_1$-$R_5$, when not comprising iodonium or protected hydroxy, is hydrogen.

* * * * *